US012779056B2

(12) United States Patent
Ohba et al.

(10) Patent No.: US 12,779,056 B2
(45) Date of Patent: Nov. 3, 2026

(54) AGENT FOR DETECTING INTERACTION BETWEEN TISSUES AND ORGANS

(71) Applicant: HAMAMATSU PHOTONICS K.K., Hamamatsu (JP)

(72) Inventors: Hiroyuki Ohba, Hamamatsu (JP); Hideo Tsukada, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 559 days.

(21) Appl. No.: 18/033,605

(22) PCT Filed: Oct. 28, 2021

(86) PCT No.: PCT/JP2021/039849
§ 371 (c)(1),
(2) Date: Apr. 25, 2023

(87) PCT Pub. No.: WO2022/092215
PCT Pub. Date: May 5, 2022

(65) Prior Publication Data
US 2023/0364273 A1 Nov. 16, 2023

(30) Foreign Application Priority Data
Oct. 29, 2020 (JP) ................................ 2020-181469

(51) Int. Cl.
*A61K 51/04* (2006.01)

(52) U.S. Cl.
CPC ................................ *A61K 51/0459* (2013.01)

(58) Field of Classification Search
CPC .................................................. A61K 51/0459
See application file for complete search history.

(56) References Cited

U.S. PATENT DOCUMENTS 9,598,399 B2 * 3/2017 Nishiyama ......... A61K 51/0459

FOREIGN PATENT DOCUMENTS

JP 2017-206457 A 11/2017
JP 2018-199626 A 12/2018

OTHER PUBLICATIONS

Mansur et al (Journal of Nuclear Medicine, vol. 66, Issue 9, 2019). (Year: 2019).*

(Continued)

*Primary Examiner* — Benjamin J Packard
(74) *Attorney, Agent, or Firm* — Faegre Drinker Biddle & Reath LLP

(57) ABSTRACT

The present invention relates to an agent for detecting an interaction between tissues and organs, the agent containing a compound represented by General Formula (1-0) as an active component.

[Chem. 1]

(1-0)

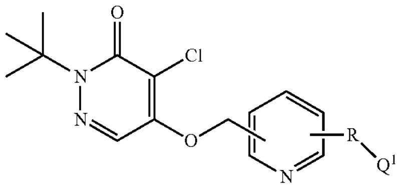

[In General Formula (1-0), R represents $—O(CH_2)_n—$, $—O(CH_2)_nOC_2H_4—$, $—CH_2O(CH_2)_n—$, or $—CH_2O(CH_2)_nOC_2H_4—$, n represents an integer of 1 to 5, and $Q^1$ represents F or $—OCH_3$].

15 Claims, 21 Drawing Sheets

(56) References Cited

OTHER PUBLICATIONS

Beeri, Michal Schnaider et al., "Type 2 Diabetes Is Negatively Associated with Alzheimer's Disease Neuropathology," The Journals of Gerontology, 60(4), 2005, pp. 471-475.
Matsuzaki, T. et al., "Insulin resistance is associated with the pathology of Alzheimer disease: The Hisayama Study," Neurology, 75(9), 2010, pp. 764-770.
Momose, Toshimitsu, "[3]"Proposals from a clinical position" toward the development of next-generation PET equipment," 2002 Next Generation PET Equipment Development Research Report [online], 2002, pp. 97-99.
Takeda, Shuko et al., "Diabetes-accelerated memory dysfunction via cerebrovascular inflammation and Abeta deposition in an Alzheimer mouse model with diabetes," Proc. Natl. Acad. Sci. USA, 107(15), 2010, pp. 7036-7041.
Tsukada, H. et al., "Novel PET Probes $^{18}$F-BCPP-EF and $^{18}$F-BCPP-BF for Mitochondrial Complex I: A PET Study in Comparison with $^{18}$F-BMS-747158-02 in Rat Brain," Journal of Nuclear Medicine, 2014; vol. 55, No. 3, pp. 473-480.
Yamamoto, Junpei et al., "Neuronal signals regulate obesity induced β-cell proliferation by FoxM1 dependent mechanism," Nature Communications, 8: 1930, 2017, pp. 1-10.
International Preliminary Report on Patentability mailed May 11, 2023 for PCT/JP2021/039849.
Wollenweber Tim et al, "Characterizing the Inflammatory Tissue Response to Acute Myocardial Infarction by Clinical Multimodality Noninvasive Imaging", Circulation. Cardiovascular Imaging, vol. 7, No. 5 DOI:10.1161/CIRCIMAGING.114.001689, Sep. 1, 2014, p. 811-p. 818, XP093330450.
European Search Report issued on Nov. 21, 2025 in counterpart EP patent application 21886332.2.

* cited by examiner (A)
ACCUMULATION IN BRAIN (SUV)
WEEKS OF AGE
Lean
Fatty
(B)
ACCUMULATION IN HEART (SUV)
WEEKS OF AGE
Lean
Fatty
(C)
ACCUMULATION IN BROWN ADIPOCYTES (SUV)
WEEKS OF AGE
Lean
Fatty
(D)
ACCUMULATION IN PANCREAS (SUV)
WEEKS OF AGE
Lean
Fatty
(E)
ACCUMULATION IN LIVER (SUV)
WEEKS OF AGE
Lean
Fatty
(F)
ACCUMULATION IN KIDNEYS (SUV)
WEEKS OF AGE
Lean
Fatty (A)

(B)

(A)

(B)

(A)

(B)

AGENT FOR DETECTING INTERACTION BETWEEN TISSUES AND ORGANS

TECHNICAL FIELD

The present invention relates to an agent for detecting an interaction between tissues and organs.

BACKGROUND ART

In recent years, it has been found that various organs that make up a living body do not function independently, but instead maintain a healthy state by maintaining a balance and functioning as a single system while closely interacting with each other. In addition, it has also been found that disturbances in this balance cause various diseases, affecting not only organs that are main causes of diseases, but also organs that are closely related to them and that recovery from a disease is aided by factors from other organs (so-called inter-organ communication).

As an example of this inter-organ communication, for example, so-called "cardiorenal syndrome" is known in which, when the function of the heart deteriorates, so does the function of the kidneys, and conversely, when the function of the kidneys deteriorates, the function of the heart also deteriorates secondarily. In addition, for example, diabetes has been shown to be an acquired risk factor for Alzheimer's dementia, and a linkage between the brain and peripheral organs (especially pancreas) is suggested (for example, Non Patent Literature 1 to 3). In addition, for example, it has been shown that the nervous system via the liver-brain-pancreas relay is important for the mechanism to proliferate the pancreatic R-cells (for example, Non Patent Literature 4), and a linkage between the liver, brain and pancreas is suggested.

CITATION LIST

Non Patent Literature

[Non Patent Literature 1] Neurology, 2010, Vol. 75, No. 9, pp. 764-770

[Non Patent Literature 2] The Journals of Gerontology, 2005, Vol. 60, No. 4, pp. 471-475

[Non Patent Literature 3] Proc. Natl. Acad. Sci. USA, 2010, Vol. 107, No. 15, pp. 7036-7041

[Non Patent Literature 4] Nature Communications, 2017, Vol. 8, Paper No. 1930

SUMMARY OF INVENTION

Technical Problem

So-called inter-organ communication is thought to be the results of interactions between organs via some network, for example, interactions between organs via physiologically active substances such as hormones and interactions between organs via the nervous system.

Conventionally, as a method for evaluating the function of each organ, an evaluation method by measuring biochemical indicators (for example, blood creatinine concentration, blood urea nitrogen (BUN) concentration, blood aspartate aminotransferase (AST) concentration, blood alanine aminotransferase (ALT) concentration, blood insulin concentration, and blood brain natriuretic peptide concentration) specific to each organ is known. However, since the time it takes for functional changes in each organ to be reflected in each biochemical indicator is different, each biochemical indicator can be affected by a plurality of factors, and the sensitivities of methods for measuring biochemical indicators are different from each other, in the conventional evaluation methods in which the biochemical indicators are used, it is impossible to accurately grasp the correlation between the functions of the organs and it is difficult to detect and evaluate interactions between the organs such as so-called inter-organ communication.

Accordingly, an object of the present invention is to provide an agent for detecting an interaction between tissues and organs, which is capable of detecting an interaction between tissues and organs of a living body such as so-called inter-organ communication. Other objects of the present invention are to provide a method for detecting an interaction between tissues and organs, provide a tissue/organ interaction detection program for detecting an interaction between tissues and organs, and provide a tissue/organ interaction detection device for detecting an interaction between tissues and organs.

Solution to Problem

The present invention relates to an agent for detecting an interaction between tissues and organs, the agent containing a compound represented by General Formula (1-0) (hereinafter also referred to as a "compound (1-0)") as an active component.

[Chem. 1]

(1-0)

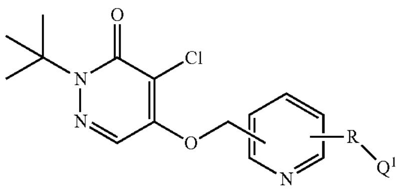

In General Formula (1-0), R represents $-O(CH_2)_n-$, $-O(CH_2)_nOC_2H_4-$, $-CH_2O(CH_2)_n-$, or $-CH_2O(CH_2)_nOC_2H_4-$, n represents an integer of 1 to 5, and $Q^1$ represents F or $-OCH_3$.

The compound (1-0) can be used for evaluating the function of mitochondrial complex I (hereinafter also referred to as "MC-I"). The compound (1-0) accumulates in each organ, and since the accumulation amount is proportional to the MC-I activity in each organ, the function of each organ can be evaluated from the amount of compound (1-0) accumulated.

In addition, as shown in examples to be described below, in tests in which normal rats (thought to be inter-tissue/organ communication models in healthy states) and diabetes model rats (thought to be inter-tissue/organ communication models in states in which hyperglycemia due to pancreatic dysfunction has induced dysfunction of other organs) were used, the amount of compound (1-0) accumulated in each tissue and organ showed a good correlation (positive correlation) between the tissues and organs. This means that interactions between the tissues and organs can be detected by determining whether there is a correlation in the function between the tissues and organs from the amount of compound (1-0) accumulated. That is, the agent for detecting an interaction between tissues and organs according to the present invention contains the compound (1-0) as an active component, and therefore can be used for detecting an interaction between the tissues and organs. Furthermore, as shown in the examples to be described below, even in a case where there is no correlation between the biochemical indicators specific to each tissue and organ, which are thought to reflect the function of each tissue and organ, the amount of compound (1-0) accumulated shows a good correlation (positive correlation) between the tissues and organs. That is, interactions between tissues and organs that cannot be detected through conventional evaluation methods using biochemical indicators can be detected using the agent for detecting an interaction between tissues and organs according to the present invention.

The present invention also relates to a method for detecting an interaction between tissues and organs, including: a step of administering the detection agent according to the present invention to a subject; a step of detecting an active component (compound (1-0)) accumulated in the tissues and/or organs to be evaluated; a step of quantitatively analyzing an amount of active component (compound (1-0)) accumulated in the tissues and/or organs to be evaluated; and a step of determining whether there is a correlation in the accumulation amount of active component (compound (1-0)) between the tissues and/or organs to be evaluated based on the quantitatively analyzed results.

The present invention also relates to a tissue/organ interaction detection device including: acquisition means for acquiring detection data on the active component (compound (1-0)) accumulated in the tissues and/or organs to be evaluated which is obtained by measuring the subject to which the detection agent according to the present invention is administered; quantitative analysis means for quantitatively analyzing the amount of the active component (compound (1-0)) accumulated in the tissues and/or organs to be evaluated from the acquired detection data; and determination means for determining whether there is a correlation in the accumulation amount of the active component (compound (1-0)) between the tissues and/or organs to be evaluated based on the quantitatively analyzed results.

The present invention also relates to a tissue/organ interaction detection program for causing a computer to function as: acquisition means for acquiring detection data on the active component (compound (1-0)) accumulated in the tissues and/or organs to be evaluated which is obtained by measuring the subject to which the detection agent according to the present invention is administered; quantitative analysis means for quantitatively analyzing the amount of the active component (compound (1-0)) accumulated in the tissues and/or organs to be evaluated from the acquired detection data; and determination means for determining whether there is a correlation in the accumulation amount of the active component (compound (1-0)) between the tissues and/or organs to be evaluated based on the quantitatively analyzed results.

Advantageous Effects of Invention

According to the present invention, it is possible to provide an agent for detecting an interaction between tissues and organs, which is capable of detecting an interaction between tissues and organs of a living body such as so-called inter-organ communication. According to the present invention, it is also possible to provide a method for detecting an interaction between tissues and organs, provide a tissue/organ interaction detection program for detecting an interaction between tissues and organs, and provide a tissue/organ interaction detection device for detecting an interaction between tissues and organs.

DESCRIPTION OF EMBODIMENT

Figure 1:
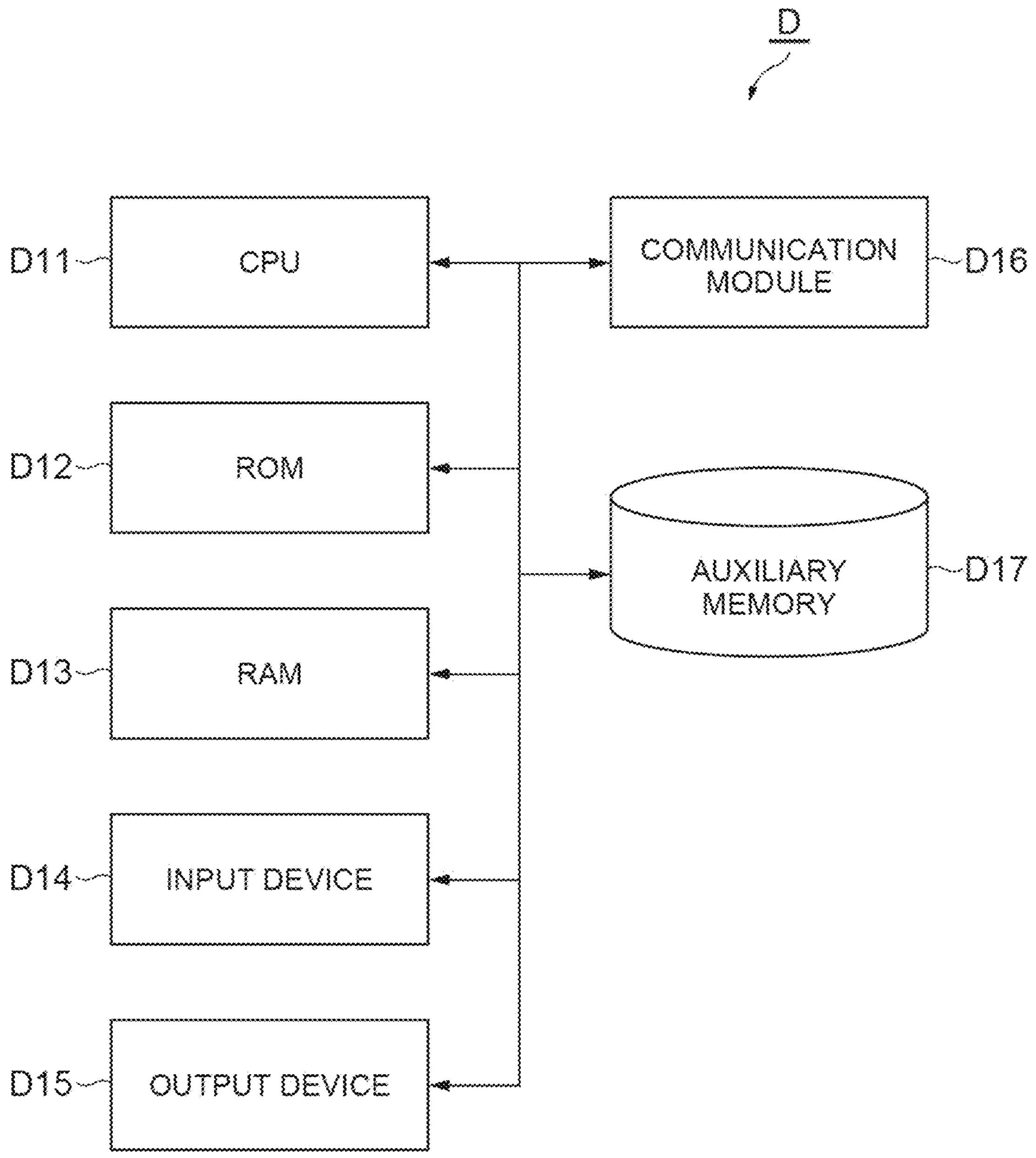
FIG. 1 is a schematic diagram illustrating a hardware configuration of a tissue/organ interaction detection device according to one embodiment.

Hereinafter, an embodiment of the present invention will be described in detail. However, the present invention is not limited to the following embodiment.

In the present specification, the term "agent for detecting an interaction between tissues and organs" means an agent that is used to detect interactions between a plurality of tissues and/or organs in a living body, regardless of whether the tissues and/or organs are in a healthy or diseased state. The agent for detecting an interaction between tissues and organs according to the present invention can evaluate the functions of a plurality of tissues and/or organs in a living body and determine whether there is a correlation between the tissues and/or organs to detect interactions between the plurality of tissues and/or organs in the living body. Accordingly, the agent for detecting an interaction between tissues and organs according to the present invention can also be regarded as an agent for detecting association between tissues and/or organs due to an interaction between the tissues and/or organs. So-called "inter-organ communication" is also included in the "association between tissues and/or organs."

[Agent for Detecting Interaction Between Tissues and Organs]

The agent for detecting an interaction between tissues and organs according to the present embodiment (hereinafter also simply referred to as a "detection agent") contains a compound represented by General Formula (1-0) as an active component.

[Chem. 2]

(1-0)

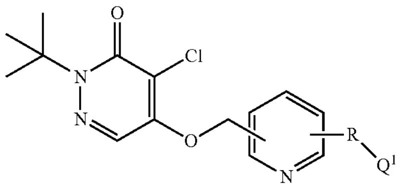

In the compound (1-0), R represents $—O(CH_2)_n—$, $—O(CH_2)$, $OC_2H_4—$, $—CH_2O(CH_2)_n—$, or $—CH_2O(CH_2)$, $OC_2H_4—$. R is preferably $—O(CH_2)_n—$ or $—O(CH_2)$, $OC_2H_4—$.

In the compound (1-0), n is an integer of 1 to 5. In the compound (1-0), in a case where R is $—O(CH_2)_n—$, n is preferably an integer of 2 to 5, more preferably an integer of 3 to 5, and still more preferably 4. In addition, in the compound (1-0), in a case where R is $-O(CH_2)$, $OC_2H_4-$, n is preferably an integer of 1 to 4, more preferably an integer of 1 to 3, and still more preferably 2.

In the compound (1-0), $Q^1$ is F or $-OCH_3$ and preferably $^{18}F$ or $-O^{11}CH_3$. Since the compound (1-0) in which $Q^1$ is $^{18}F$ or $-O^{11}CH_3$ can release positrons, it is suitable as a labeled compound (PET probe) for use in a PET method. In addition, in a case where $Q^1$ is $-O^{11}CH_3$, the half-life is as short as 20 minutes, so it is also possible to perform measurements multiple times on the same subject in one day. In a case where $Q^1$ is $^{18}F$, a half-life is 110 minutes, which is longer than that of $-O^{11}CH_3$. Therefore, it is possible to lengthen the time for one measurement and to deliver a PET probe labeled and synthesized at a facility with a cyclotron to another facility with a PET camera.

A binding site of R in a pyridine ring and a binding site of $-OCH_2-$ which binds to a pyridazine ring are not particularly limited, but the binding site of $-OCH_2-$ binding to a pyridazine ring is preferably at position 5 of the pyridine ring and the binding site of R is preferably at position 2 of the pyridine ring. A compound represented by General Formula (1-0') shown below (hereinafter also referred to as a "compound (1-0')") has a structural formula in which the binding site of $-OCH_2-$ binding to a pyridazine ring is at position 5 of the pyridine ring and the binding site of R is at position 2 of the pyridine ring.

[Chem. 3]

(1-0')

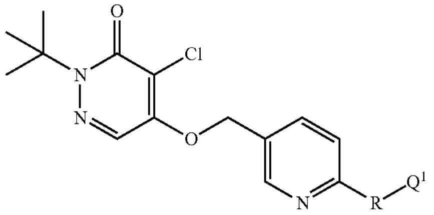

In General Formula (1-0'), R, n, and $Q^1$ are synonymous with R, n, and $Q^1$ in General Formula (1-0).

In view of making it more suitable for detecting an interaction between tissues and organs, the compound (1-0) is preferably a compound represented by General Formula (1-0") (hereinafter also referred to as a "compound (1-0")") or a compound represented by General Formula (1-0"') (hereinafter also referred to as a "compound (1-0"')") and more preferably a compound represented by Formula (1") (hereinafter also referred to as a "compound (1")") or a compound represented by Formula (1"') (hereinafter also referred to as a "compound (1"')").

[Chem. 4]

(1-0")

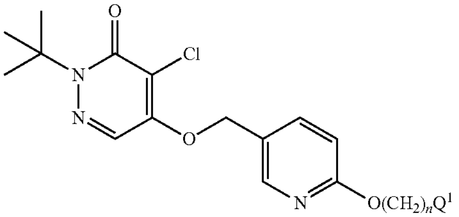

[Chem. 5]

(1-0"')

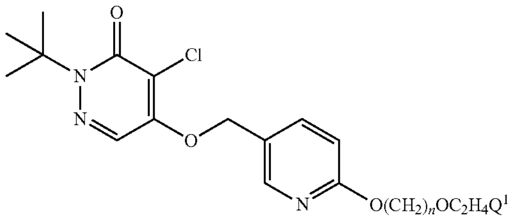

In General Formulae (1-0") and (1-0"'), n and $Q^1$ are synonymous with n and $Q^1$ in General Formula (1-0).

[Chem. 6]

(1")

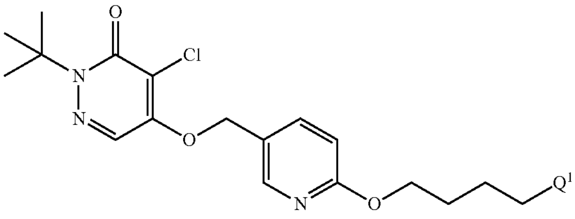

[Chem. 7]

(1"')

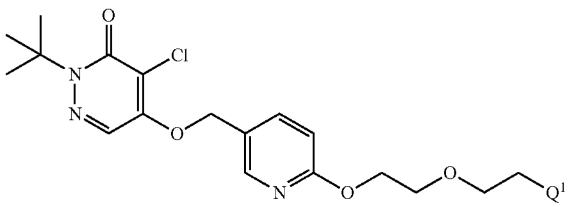

In Formula (1") and (1"'), Q is synonymous with $Q^1$ in General Formula (1-0).

The compound (1-0) can be synthesized, for example, from a corresponding precursor. The same applies to the compound (1-0'), the compound (1-0"), the compound (1-0"'), the compound (1"), and the compound (1"').

Examples of precursors corresponding to the compound (1-0) include a compound represented by General Formula (2-0) below (hereinafter also referred to as a "compound (2-0)"). Examples of precursors corresponding to the compound (1-0'), the compound (1-0"), the compound (1-0"'), the compound (1"), and the compound (1"') include compounds in which, in the compound (2-0), R, the binding site of R in a pyridine ring, and the binding site of $-OCH_2-$ binding to a pyridazine ring are the same as those in the compound (1-0'), the compound (1-0"), the compound (1-0"'), the compound (1"), and the compound (1"').

[Chem. 8]

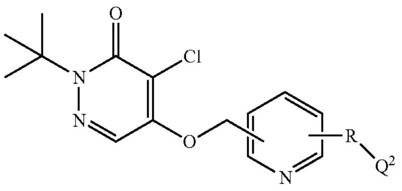

(2-0)

In General Formula (2-0), R is synonymous with R in General Formula (1-0). $Q^2$ represents a removable substituent (a substituted sulfonyloxy group, a halogen atom, or a hydroxyl group).

Examples of substituted sulfonyloxy groups include a tosyloxy group (-OTs), a methanesulfonyloxy group (-OMs), a trifluoromethanesulfonyloxy group (-OTf), and a nitrobenzenesulfonyloxy group (-ONs), and -OTs is preferably used.

Examples of halogen atoms include fluorine, chlorine, bromine, and iodine.

A precursor can be synthesized through, for example, a method disclosed in PCT International Publication No. WO2014/30709.

Since the compound (1-0) accumulates in each tissue and organ specifically for MC-I, the accumulation amount changes in correlation with the degree of the function of each tissue and organ. That is, the accumulation amount of compound (1-0) decreases when the function of each tissue and organ deteriorates, and the accumulation amount of compound (1-0) increases when the function of each tissue and organ is enhanced. Accordingly, the detection agent according to the present embodiment can evaluate the function of each tissue and organ by measuring the amount of compound (1-0) accumulated and determine whether there is a correlation in the function between the plurality of tissues and organs to detect interactions between the plurality of tissues and/or organs in a living body.

The measurement of the accumulation amount of compound (1-0) is not limited to this, and can be carried out such that, for example, the compound (1-0) is bound to a fluorescent dye or the like or labeled with a single photon nuclide (such as $^{123}I$, $^{99m}Tc$) or a positron nuclide to form a labeled compound, and the label is detected. The positron labeling can be performed, for example, by setting $Q^1$ of the compound (1-0) to $—O^{11}CH_3$ or $^{18}F$. In the case of the positron labeling, biodistribution of the compound (1-0) can be quantitatively imaged over time by measuring annihilation radiation with a device used for a PET method.

In addition, the amount of compound (1-0) accumulated can be measured not only by the above-described diagnostic imaging method but also by a method for measuring radioactivity or the like of cells, tissues, and organs collected from a living body, to which a labeled compound is administered, through techniques such as dissection or biopsy. Even in this case, the correlation between tissues and organs can be evaluated in the same manner as in the diagnostic imaging method.

The detection agent according to the present embodiment can be produced, for example, by dissolving the compound (1-0) in an arbitrary buffer solution. In this case, the detection agent according to the present embodiment may be provided as a solution and contain other components such as a surfactant, a preservative, and a stabilizer in addition to the buffer component.

[Method for Detecting Interaction Between Tissues and Organs]

A method for detecting an interaction between tissues and organs according to the present embodiment includes: a step of administering the detection agent according to the present invention to a subject; a step of detecting a compound (1-0) accumulated in the tissues and/or organs to be evaluated; a step of quantitatively analyzing an amount of compound (1-0) accumulated in the tissues and/or organs to be evaluated; and a step of analyzing whether there is a correlation in the accumulation amount of compound (1-0) between the tissues and/or organs to be evaluated based on the quantitatively analyzed results.

Examples of subjects include humans, monkeys, mice, and rats, but are not limited thereto.

A method for administering a detection agent to a subject is not particularly limited as long as the compound (1-0) reaches tissues and organs to be evaluated, but is usually intravenous administration.

The dose of a detection agent is not particularly limited as long as it is a sufficient dose to detect the compound (1-0) in tissues and organs to be evaluated, but may be appropriately set according to subjects to which it is administered and methods for detecting the compound (1-0). For example, in a case where the compound (1-0) is detected with a device used for a PET method using a detection agent containing a compound (1-0) in which $Q^1$ is $^{18}F$ or $—O^{11}CH_3$, the dose (hereinafter also referred to as an "amount of radioactivity administered") of the detection agent may be 1 MBq/kg body weight to 1,000 MBq/kg body weight. The specific radioactivity of the compound (1-0) may be 10 to 10,000 GBq/μmol. In addition, the amount of radioactivity administered of a detection agent depends on the sensitivity of a PET camera used and the volume of an individual subject, but about 200 to 500 MBq/kg body weight thereof is administered as 0.1 to 0.5 mL of a physiological saline solution for rodents (mice and rats). In a case of non-human primates (monkeys), 40 to 200 MBq/kg body weight thereof is administered as 0.5 to 2 mL of physiological saline, and in a case of humans, 2 to 10 MBq/kg body weight thereof is administered as 1 to 5 mL of a physiological saline solution.

The method for detecting the compound (1-0) accumulated in tissues and/or organs to be evaluated is not particularly limited, and can be carried out according to well-known methods. For example, in a case where a detection agent containing a compound (1-0) in which $Q^1$ is $^{18}F$ or $—O^{11}CH_3$ is used, the compound (1-0) can be detected through a PET method. The measurement method in the PET method is not particularly limited, and can be carried out according to well-known methods. In addition, for example, as a measurement method in the PET method, dynamic measurement may be performed for 60 minutes immediately after administering a detection agent, or PET measurement may be performed for 10 to 20 minutes after administering a detection agent and waiting for 30 to 40 minutes to allow sufficient accumulation of the compound (1-0) in tissues and/or organs to be evaluated.

The method for quantitatively analyzing the amount of compound (1-0) accumulated in tissues and/or organs to be evaluated is not particularly limited, and can be carried out according to well-known methods. For example, the following method is exemplified. First, an integrated image of a compound (1-0) obtained through a PET method and a morphological image of tissues and/or organs obtained through CT measurement or the like are superimposed to identify a PET image of the tissues and/or organs. Next, a region of interest on the PET image of the tissues and/or organs is set, and a value normalized by the amount of radioactivity administered and the body weight of an individual subject is defined as an amount of compound (1-0) accumulated in the tissues and/or organs. In addition, an image obtained by a PET method in which a probe capable of detecting the tissues and/or organs is used may be used instead of the morphological image of the tissues and/or organs.

In addition, as a method for detecting and quantitatively analyzing a compound (1-0) accumulated in tissues and/or organs to be evaluated, it is also possible to employ, for example, the method for measuring radioactivity or the like of cells, tissues, and organs collected from a living body, to which a labeled compound is administered, through techniques such as dissection or biopsy. The method for measuring radioactivity or the like of cells, tissues, and organs collected is not particularly limited, and can be carried out according to well-known methods. Specifically, for example, the radioactivity of cells, tissues, and organs collected can be measured using a radioactivity measuring device. In addition, a value obtained by normalizing the obtained measurement value of the radioactivity by the amount of radioactivity administered and the body weight of an individual subject is defined as an amount of compound (1-0) accumulated in the tissues and/or organs.

A method for determining whether there is a correlation in the accumulation amount of compound (1-0) between the tissues and/or organs to be evaluated is not particularly limited as long as it can determine whether there is a correlation in the accumulation amount of compound (1-0) between a plurality of tissues and/or organs to be evaluated. Specifically, for example, in the plurality of tissues and/or organs to be evaluated, a correlation equation may be calculated in advance from data on the accumulation amount for which a correlation is recognized and used as a reference equation to determine whether there is a correlation according to the degree of divergence between the data on the accumulation amount measured in the subject and the reference equation. In this case, in a case where, for example, the reference equation is represented by $y=ax+b$ (x and y are the accumulation amount in any tissue or organ, and a and b are constants), for example, it may be determined that there is a correlation when $ax+0.9b\leq y\leq ax+1.1b$ is satisfied, it may be determined that there is a correlation when $ax+0.95b\leq y\leq ax+1.05b$ is satisfied, and it may be determined that there is a correlation when $ax+0.97b\leq y\leq ax+1.03b$ is satisfied. In addition, machine learning (for example, deep learning) may be applied to data on the amount of compound (1-0) accumulated in a plurality of tissues and/or organs of a large number of samples to determine whether there is a correlation in the accumulation amount of compound (1-0) between arbitrary tissues and organs through the machine learning.

Tissues and/or organs to be evaluated are not particularly limited as the compound (1-0) is accumulated specifically for MC-I (that is, it can be accumulated in any organ), and specific examples thereof include the brain, the heart, the liver, the pancreas, the kidneys, brown adipocytes (brown adipose tissue), and muscles.

The present invention can also be regarded as a data collection method for detecting an interaction between tissues and organs, the method including: a step of quantitatively analyzing the amount of compound (1-0) accumulated in tissues and/or organs to be evaluated from detection data on the compound (1-0) which is accumulated in the tissues and/or organs to be evaluated and obtained by measuring the subject to which the detection agent according to the present invention is administered; a step of determining whether there is a correlation in the accumulation amount of compound (1-0) between the tissues and/or organs to be evaluated based on the quantitatively analyzed results. The data which indicates the presence or absence of a correlation in the accumulation amount between the tissues and organs and is obtained in the determination step can be used for detecting an interaction between the tissues and organs.

[Tissue/Organ Interaction Detection Device]

A tissue/organ interaction detection device according to the present embodiment includes: acquisition means for acquiring detection data on the active component accumulated in the tissues and/or organs to be evaluated which is obtained by measuring the subject to which the detection agent according to the present invention is administered; quantitative analysis means for quantitatively analyzing the amount of the active component accumulated in the tissues and/or organs to be evaluated from the acquired detection data; and determination means for determining whether there is a correlation in the accumulation amount of the active component between the tissues and/or organs to be evaluated based on the quantitatively analyzed results.

Figure 2:
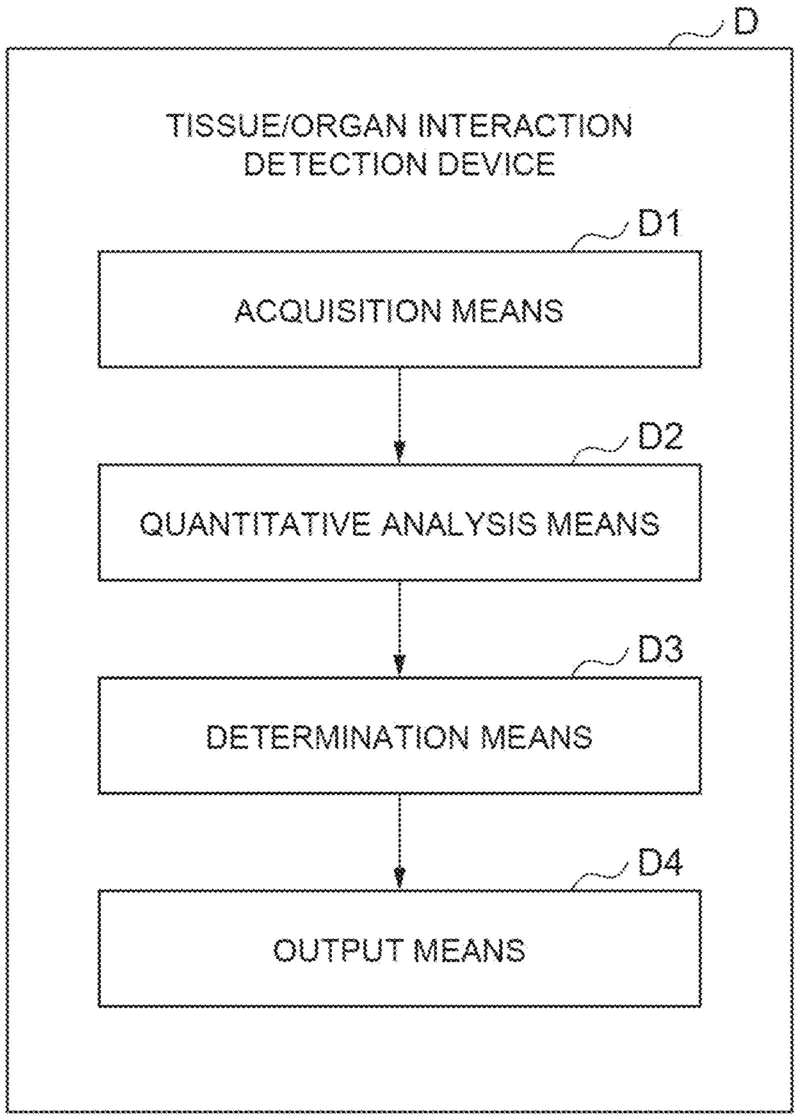
FIG. 2 is a schematic diagram illustrating a functional configuration of a tissue/organ interaction detection device according to one embodiment.

The configuration of a tissue/organ interaction detection device D according to the present embodiment will be described. FIG. 1 is a schematic diagram illustrating a hardware configuration of the tissue/organ interaction detection device D according to one embodiment. FIG. 2 is a schematic diagram illustrating a functional configuration of the tissue/organ interaction detection device D according to one embodiment.

As shown in FIG. 1, the tissue/organ interaction detection device D is physically configured as a usual computer including: main memories such as a CPU D11, ROM D12, and RAM D13; input devices D14 such as a keyboard, a mouse and a touch screen; an output device D15 such as a display (including a touch screen); a communication module D16 such as a network card for transmitting and receiving data to and from other devices; and an auxiliary memory D17 such as a hard disk. Each function of the tissue/organ interaction detection device D to be described below is realized by loading predetermined computer software onto hardware such as the CPU D11, ROM D12, and RAM D13, operating the input devices D14, the output device D15, and the communication module D16 under control of the CPU D11, and reading and writing data in the main memories D12 and D13 and the auxiliary memory D17.

As shown in FIG. 2, the tissue/organ interaction detection device D includes acquisition means D1, quantitative analysis means D2, determination means D3, and output means D4 as functional constituent elements.

The acquisition means D1 acquires detection data on the active component accumulated in the tissues and/or organs to be evaluated which is obtained by measuring the subject to which the above-described detection agent according to the present invention is administered. The detection data may be integrated image data on an active component which is in a region containing tissues and/or organs to be evaluated and contains information on the signal intensity (for example, fluorescence intensity and radiation intensity) emitted from a label of the active component.

The quantitative analysis means D2 quantitatively analyzes the amount of the active component accumulated in the tissues and/or organs to be evaluated from the detection data acquired by the acquisition means D1. In the quantitative analysis, for example, the integrated image of the active component and the morphological image of the tissues and/or organs obtained through the CT measurement or the like are superimposed to identify the tissues and/or organs in the integrated image of the active component, and a value obtained by normalizing the signal intensity (for example, fluorescence intensity and radiation intensity) in the identified region by the body weight of the individual subject is calculated as data on the amount of active component accumulated in the tissues and/or organs. The morphological image data on the tissues and/or organs and the data on the amount of radioactivity administered and the body weight of the individual subject may be acquired in advance by the acquisition means D1.

The determination means D3 determines whether there is a correlation in the accumulation amount of the active component between the tissues and/or organs to be evaluated based on the data on the amount of active component accumulated in the tissues and/or organs which is obtained by the quantitative analysis means D2. The presence or absence of a correlation may be determined, for example, by determining the degree of divergence between the reference equation and the results obtained by storing a correlation equation calculated in advance from the data on the accumulation amount, for which a correlation is recognized in a plurality of tissues and/or organs to be evaluated as a reference equation, in the main memories D12 and D13 or the auxiliary memory D17 and quantitatively analyzing the stored data using the quantitative analysis means D2. In the determination of the degree of the divergence, in a case where, for example, the reference equation is represented by $y=ax+b$ (x and y are the accumulation amount in any tissue or organ, and a and b are constants), for example, it may be determined that there is a correlation when $ax+0.9b \leq y \leq ax+1.1b$ is satisfied, it may be determined that there is a correlation when $ax+0.95b \leq y \leq ax+1.05b$ is satisfied, and it may be determined that there is a correlation when $ax+0.97b \leq y \leq ax+1.03b$ is satisfied. In addition, for example, in a case where the presence or absence of a correlation is determined through machine learning (for example, deep learning), results learned in advance through machine learning may be stored in the main memories D12 and D13 or the auxiliary memory D17 and the data on the amount of active component accumulated in the tissues and/or organs which is obtained by the quantitative analysis means D2 to determine the presence or absence of a correlation.

The output means D4 outputs the results determined by the determination means D3. The results may be output to an output device, output from a communication module to another device, or output to an auxiliary memory for recording.

[Tissue/Organ Interaction Detection Program]

The tissue/organ interaction detection program according to the present embodiment causes a computer to function as the acquisition means D1, the quantitative analysis means D2, the determination means D3, and the output means D4 described above. The computer operates as the tissue/organ interaction detection device D by loading the tissue/organ interaction detection program into the computer. The tissue/organ interaction detection program is recorded in, for example, a computer-readable recording medium, and provided. The recording medium may be a non-transitory recording medium. Examples of recording media include recording media such as a flexible disk, CD, and DVD, recording media such as ROM, and semiconductor memories.

Figure 3:
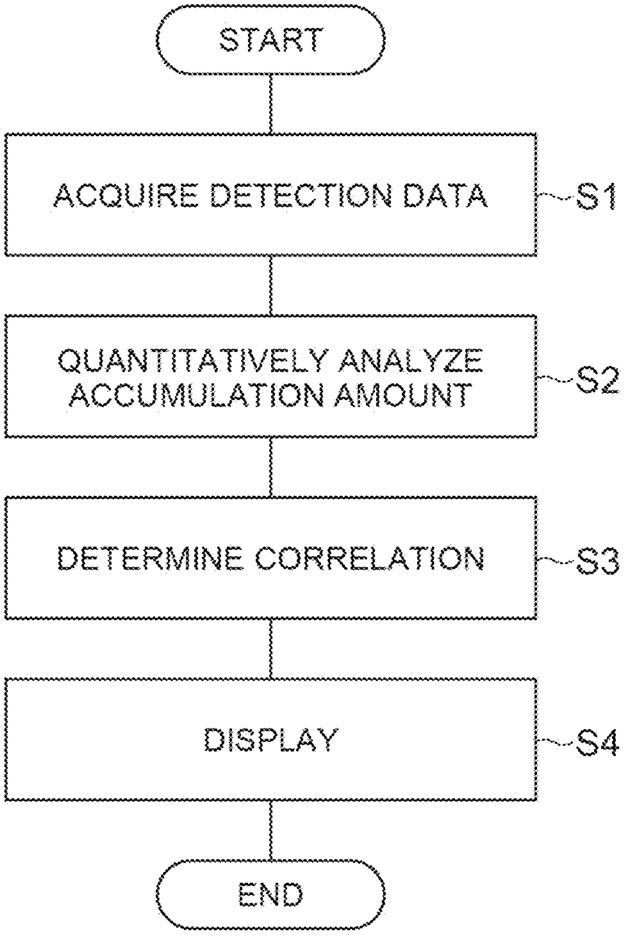
FIG. 3 is a flowchart of a method for detecting an interaction between tissues and organs according to one embodiment.

The method for detecting an interaction between tissues and organs which is performed by the tissue/organ interaction detection device D will be described. FIG. 3 is a flowchart of a method for detecting an interaction between tissues and organs according to one embodiment.

[Acquisition Step S1]

First, the acquisition means D1 acquires detection data on the active component accumulated in the tissues and/or organs to be evaluated which is obtained by measuring the subject to which the above-described detection agent according to the present invention is administered. The morphological image data on the tissues and/or organs and the data on the amount of radioactivity administered and the body weight of the individual subject may be acquired as necessary by the acquisition means D1.

[Quantitative Analysis Step S2]

Next, the quantitative analysis means D2 quantitatively analyzes the amount of active component accumulated in the tissues and/or organs to be evaluated from the acquired detection data.

[Determination Step S3]

Next, the determination means D3 determines whether there is a correlation in the accumulation amount of the active component between the tissues and/or organs to be evaluated based on the data on the amount of active component accumulated in the tissues and/or organs which is calculated in Quantitative Analysis Step S2.

[Display Step S4]

Next, the output means D4 outputs the results determined in Determination Step S3 (for example, displays the results on an output device or the like). For example, data indicating whether tissues and/or organs to be evaluated interact, data on the amount of active component accumulated in the tissues and/or organs, and data on a graph (image) in which the accumulation amount data and the reference equation are plotted are output by the output means D4.

EXAMPLES

Hereinafter, the present invention will be described in more detail based on examples. However, the present invention is not limited to thereto.

Test Example 1: Detection of Interaction Between Tissues and Organs (1)

(Synthesis of PET probe)

[$^{18}$F]BCPP-BF represented by the following formula was synthesized according to the method disclosed in Non Patent Literature (J. Labeled Comp. Radiopharm., 2013, Vol. 56, No. 11, pp. 553-561). The final product obtained had a radiochemical purity of 99.0% and a specific radioactivity of 73.4 GBq/μmol.

[Chem. 9]

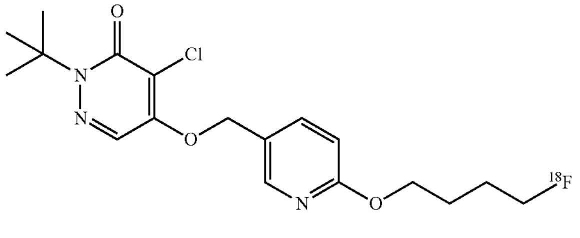

In addition, a probe (D-[$^{11}$C]MT) that recognizes amino acid transporter (LAT-1) highly expressed in pancreases of small animals was prepared to specify the position of the pancreas. D-[$^{11}$C]MT was synthesized through a method disclosed in Example 1 of PCT International Publication No. WO2005/115971. The final product obtained had a radiochemical purity of 99.0% and a specific radioactivity of 66.4 GBq/μmol.

(Evaluation of Function of Each Tissue and Organ in Type 2 Diabetes Model Rats)

Male Zucker Leprfa/Leprfa rats (hereinafter also referred to as "fatty rats") that develop pathological conditions similar to type 2 diabetes of human adults and male Zucker Leprfa/+ rats (hereinafter also referred to as "lean rats") as controls thereof were purchased from Charles River Laboratories Japan, Inc., and used for PET measurement at 5, 8, 16, and 26 weeks of age, and the amount of [$^{18}$F]BCPP-BF accumulated in each tissue and organ (brain, heart, kidneys, liver, and brown adipocytes (brown adipose tissue)) was measured.

The rats were anesthetized with isoflurane and fixed in a gantry of an animal PET camera (SHR-38000, manufactured by Hamamatsu Photonics K.K.). After 15-minute transmission measurement was carried out for absorption correction, about 20 MBq/0.5 mL of D-[$^{11}$C]MT was administered to the rats via the tail vein and 60-minute emission measurement was carried out. Subsequently, about 20 MBq/0.5 mL [$^{18}$F]BCPP-BF was administered to the rats via the tail vein, and 60-minute emission measurement was carried out.

After the completion of the PET measurement, a region of interest was set on the pancreas identified by an integrated PET image 40 to 60 minutes after the administration of D-[$^{11}$C]MT, and the amount of [$^{18}$F]BCPP-BF accumulated in the region of interest was calculated. Subsequently, the calculated accumulation amount was normalized by the amount of radioactivity administered and the body weight of each individual and defined as an amount (amount (SUV) of radioactivity accumulated) of [$^{18}$F]BCPP-BF accumulated in the pancreas. For tissues and organs other than the pancreas, a region of interest was set for each tissue and organ identified by an integrated PET image of [$^{18}$F]BCPP-BF, and the amount (SUV) of radioactivity accumulated was calculated in the same manner as for the pancreas. The amount (SUV) of radioactivity accumulated in the brain was calculated by excising the brains from the rats immediately after the PET measurement. In addition, the presence or absence of a correlation between the tissues and organs with respect to the amount (SUV) of radioactivity accumulated of [$^{18}$F]BCPP-BF in the tissues and organs was evaluated.

(Measurement of Biochemical Indicator)

Blood was collected from the rats immediately after the PET measurement, and the blood BUN concentration, the blood creatinine concentration, the blood AST concentration, the blood ALT concentration, and the blood insulin concentration were measured with a biochemical automatic analyzer (7180 manufactured by Hitachi High-Tech Corporation). The blood BUN concentration, the blood creatinine concentration, the blood AST concentration, the blood ALT concentration, and the blood insulin concentration were used as biochemical indicators that reflect the function of the pancreas, the kidneys, and the liver.

(Results)

Figure 4:
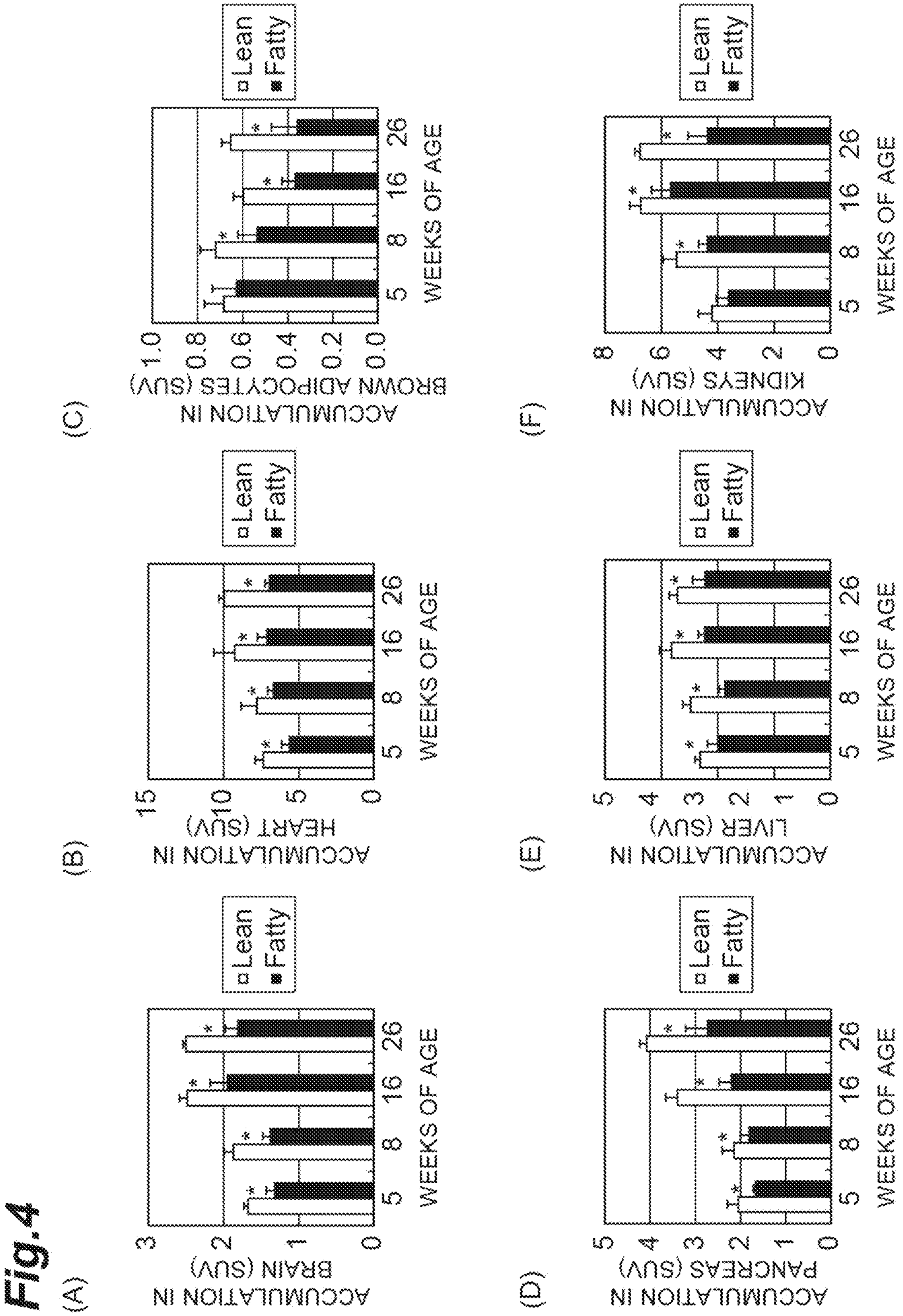
FIG. 4 is a graph illustrating the amount of [$^{18}$F]BCPP-BF accumulated in each tissue and organ (brain, heart, brown adipocytes, pancreas, liver, and kidneys).
Figure 5:
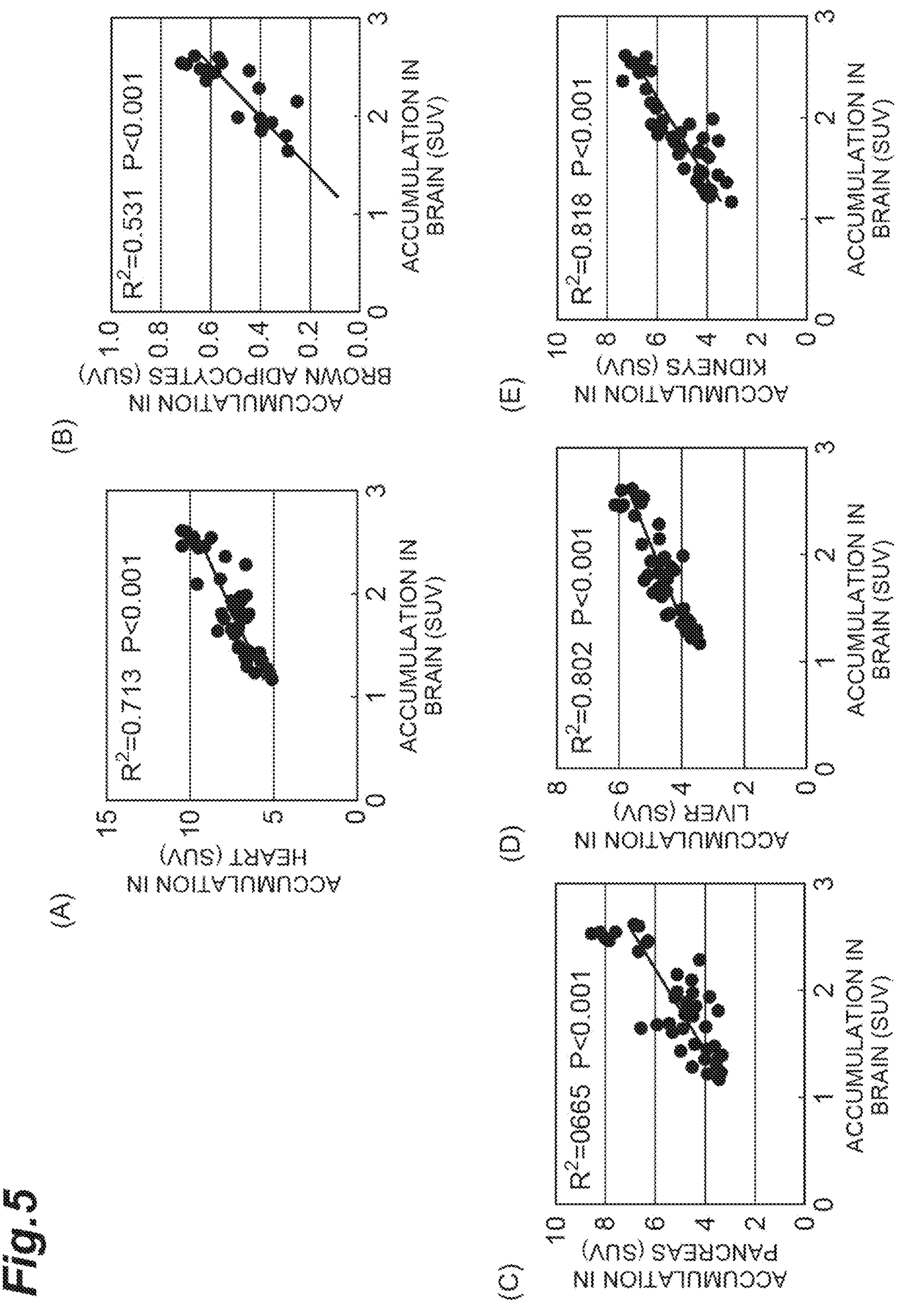
FIG. 5(A) is a graph illustrating a relationship in the accumulation amount of [$^{18}$F]BCPP-BF between the brain and the heart.
FIG. 5(B) is a graph illustrating a relationship in the accumulation amount of [$^{18}$F]BCPP-BF between the brain and brown adipocytes.
FIG. 5(C) is a graph illustrating a relationship in the accumulation amount of [$^{18}$F]BCPP-BF between the brain and the pancreas.
FIG. 5(D) is a graph illustrating a relationship in the accumulation amount of [$^{18}$F]BCPP-BF between the brain and the liver.
FIG. 5(E) is a graph illustrating a relationship in the accumulation amount of [$^{18}$F]BCPP-BF between the brain and the kidneys.
Figure 6:
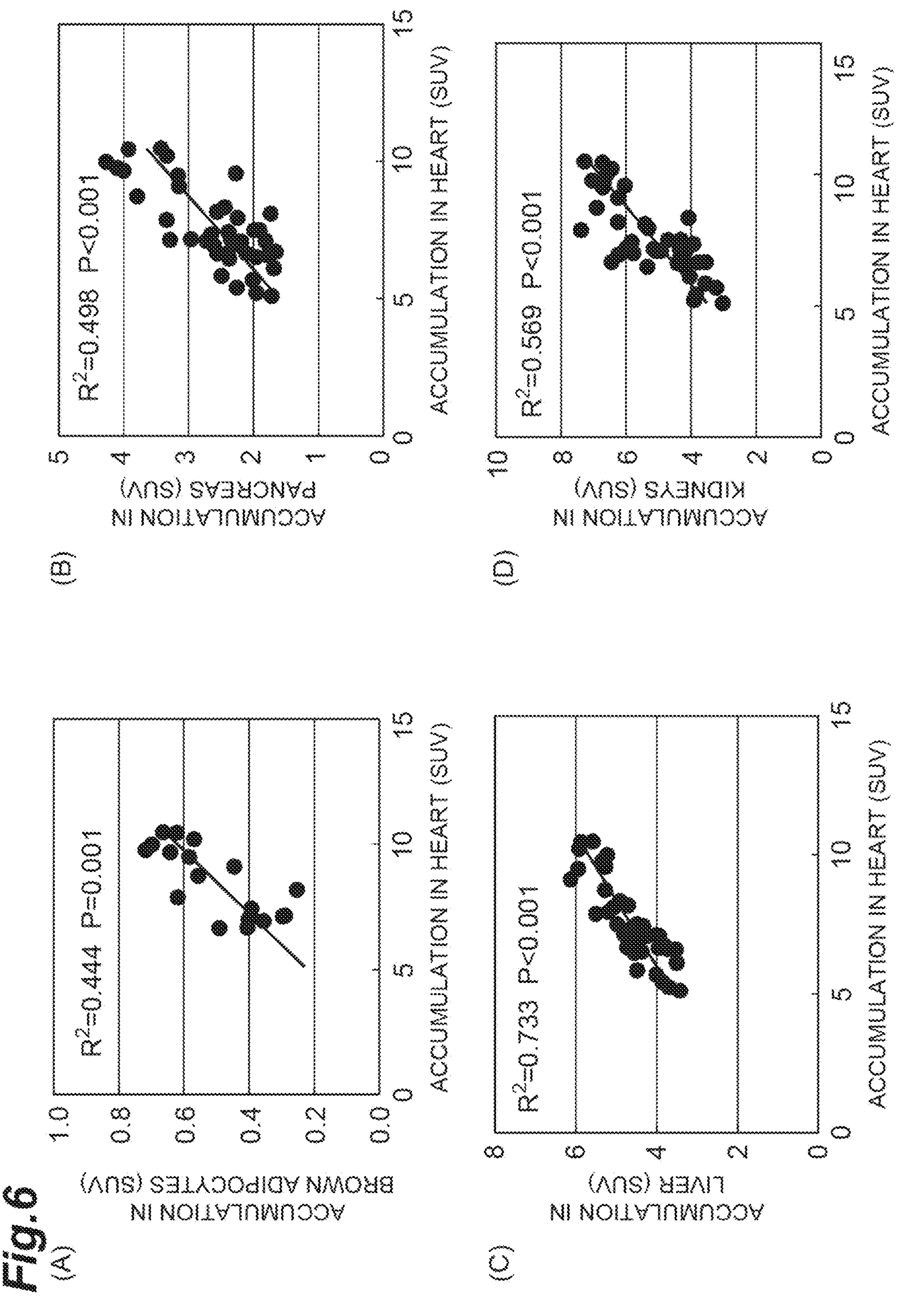
FIG. 6(A) is a graph illustrating a relationship in the accumulation amount of [$^{18}$F]BCPP-BF between the heart and brown adipocytes.
FIG. 6(B) is a graph illustrating a relationship in the accumulation amount of [$^{18}$F]BCPP-BF between the heart and the pancreas.
FIG. 6(C) is a graph illustrating a relationship in the accumulation amount of [$^{18}$F]BCPP-BF between the heart and the liver.
FIG. 6(D) is a graph illustrating a relationship in the accumulation amount of [$^{18}$F]BCPP-BF between the heart and the kidneys.
Figure 7:
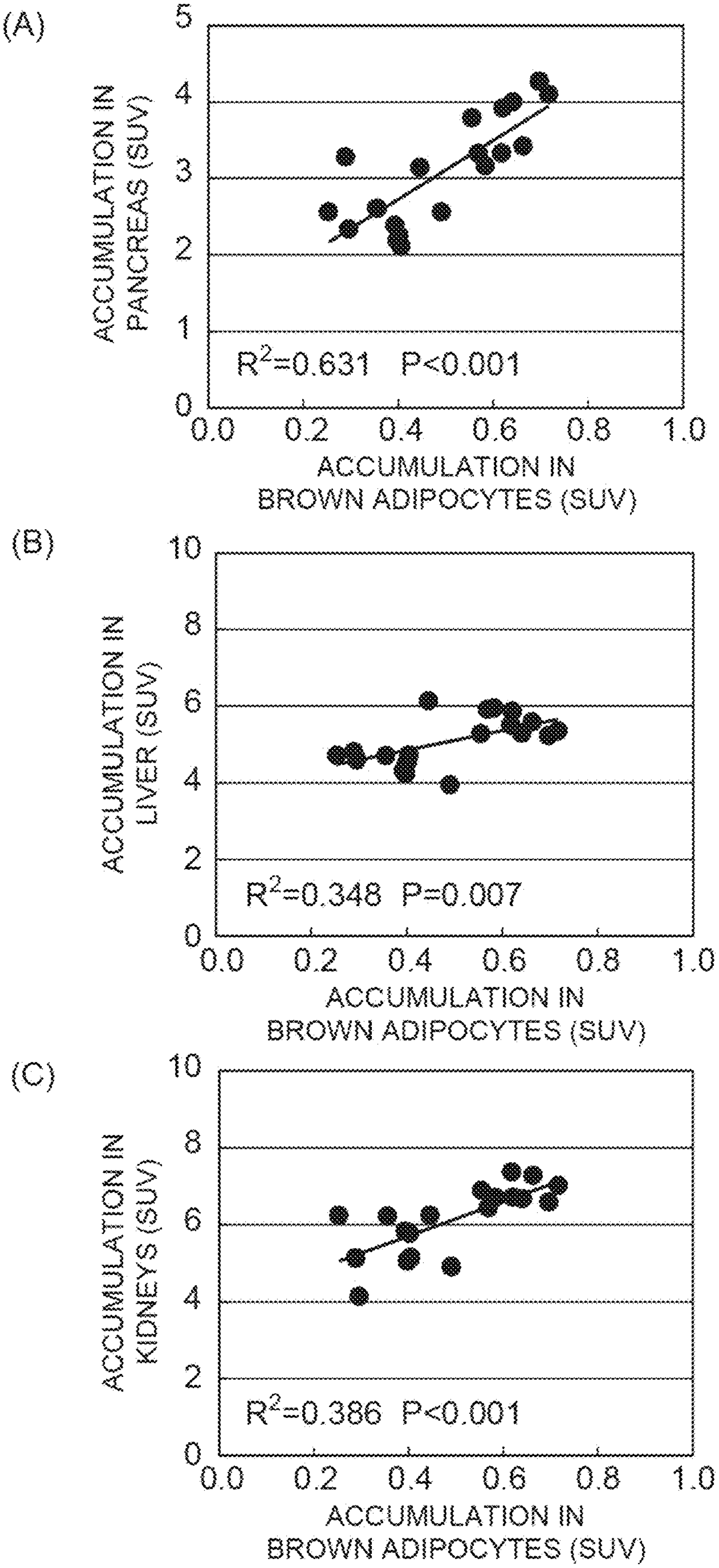
FIG. 7(A) is a graph illustrating a relationship in the accumulation amount of [$^{18}$F]BCPP-BF between brown adipocytes and the pancreas.
FIG. 7(B) is a graph illustrating a relationship in the accumulation amount of [$^{18}$F]BCPP-BF between brown adipocytes and the liver.
FIG. 7(C) is a graph illustrating a relationship in the accumulation amount of [$^{18}$F]BCPP-BF between brown adipocytes and the kidneys.
Figure 8:
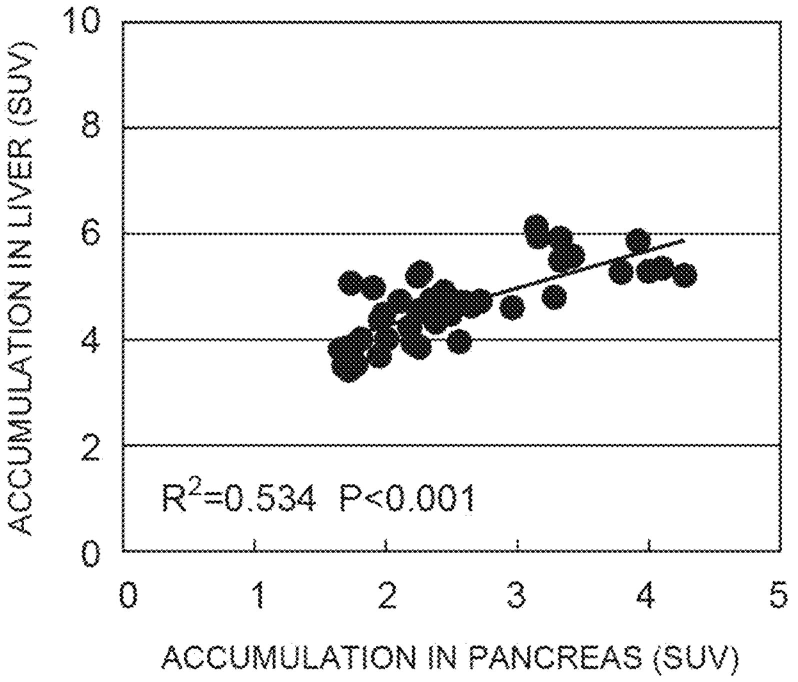
FIG. 8(A) is a graph illustrating a relationship in the accumulation amount of [$^{18}$F]BCPP-BF between the pancreas and the liver.
FIG. 8(B) is a graph illustrating a relationship in the accumulation amount of [$^{18}$F]BCPP-BF between the pancreas and the kidneys.
Figure 8:
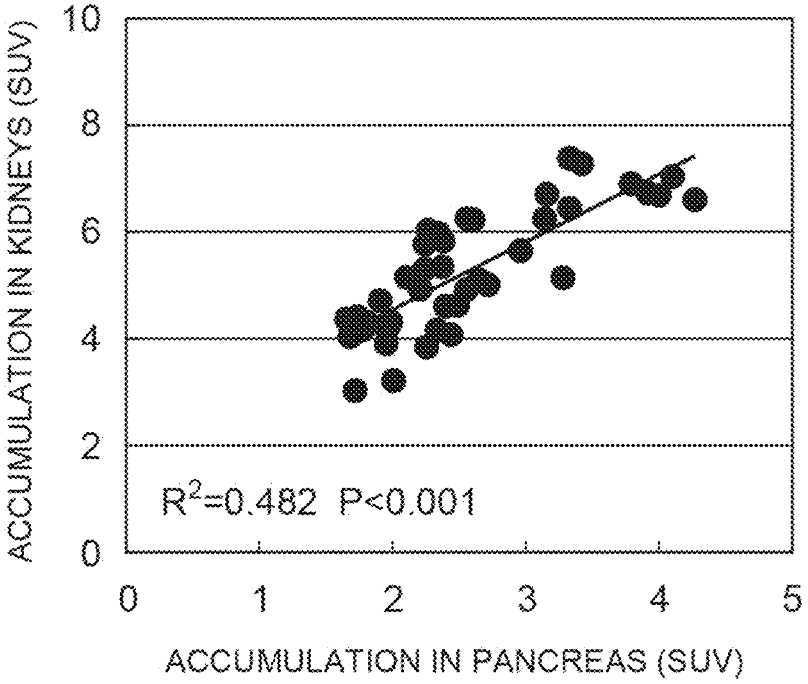

FIG. 4 is a graph illustrating the amount of [$^{18}$F]BCPP-BF accumulated in each tissue and organ (brain, heart, brown adipocytes, pancreas, liver, and kidneys). Except for brown adipocytes (tissue) and the kidneys at 5 weeks of age, the accumulation amount in fatty rats was significantly lower than that in lean rats at all weeks of age and organs. It is thought that this indicates that the function of each tissue and organ deteriorated with the onset of diabetes.

FIGS. 5 to 9 are graphs illustrating relationships in the accumulation amount of [$^{18}$F]BCPP-BF between tissues and organs. In FIGS. 5 to 9, the accumulation amount in the fatty rats and the accumulation amount in the lean rats are plotted without distinction.

Figure 9:
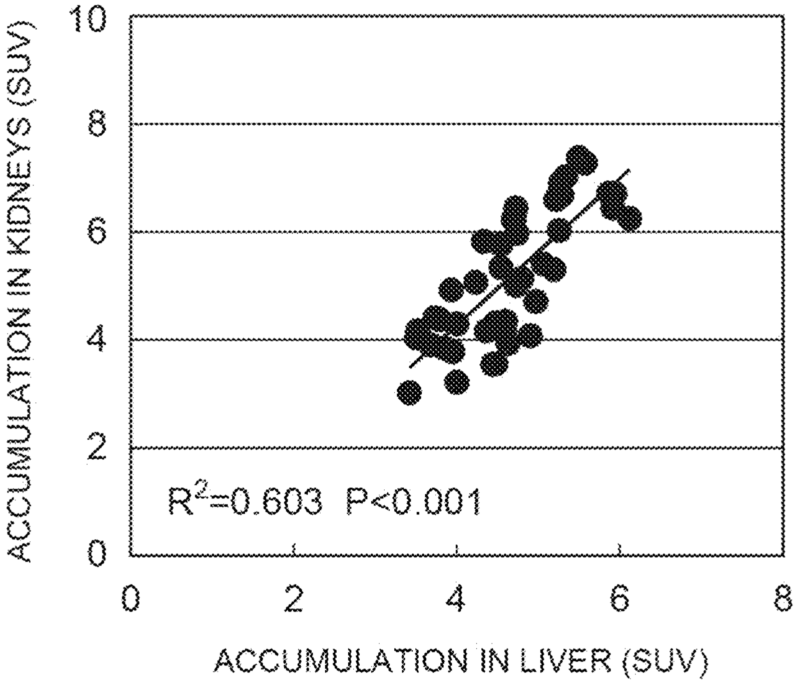
FIG. 9 is a graph illustrating a relationship in the accumulation amount of [$^{18}$F]BCPP-BF between the liver and the kidneys.

FIG. 5(A) is a graph illustrating a relationship in the accumulation amount of [$^{18}$F]BCPP-BF between the brain and the heart. FIG. 5(B) is a graph illustrating a relationship in the accumulation amount of [$^{18}$F]BCPP-BF between the brain and brown adipocytes. FIG. 5(C) is a graph illustrating a relationship in the accumulation amount of [$^{18}$F]BCPP-BF between the brain and the pancreas. FIG. 5(D) is a graph illustrating a relationship in the accumulation amount of [$^{18}$F]BCPP-BF between the brain and the liver. FIG. 5(E) is a graph illustrating a relationship in the accumulation amount of [$^{18}$F]BCPP-BF between the brain and the kidneys. FIG. 6(A) is a graph illustrating a relationship in the accumulation amount of [$^{18}$F]BCPP-BF between the heart and brown adipocytes. FIG. 6(B) is a graph illustrating a relationship in the accumulation amount of [$^{18}$F]BCPP-BF between the heart and the pancreas. FIG. 6(C) is a graph illustrating a relationship in the accumulation amount of [$^{18}$F]BCPP-BF between the heart and the liver. FIG. 6(D) is a graph illustrating a relationship in the accumulation amount of [$^{18}$F]BCPP-BF between the heart and the kidneys. FIG. 7(A) is a graph illustrating a relationship in the accumulation amount of [$^{18}$F]BCPP-BF between brown adipocytes and the pancreas. FIG. 7(B) is a graph illustrating a relationship in the accumulation amount of [$^{18}$F]BCPP-BF between brown adipocytes and the liver. FIG. 7(C) is a graph illustrating a relationship in the accumulation amount of [$^{18}$F]BCPP-BF between brown adipocytes and the kidneys. FIG. 8(A) is a graph illustrating a relationship in the accumulation amount of [$^{18}$F]BCPP-BF between the pancreas and the liver. FIG. 8(B) is a graph illustrating a relationship in the accumulation amount of [$^{18}$F]BCPP-BF between the pancreas and the kidneys. FIG. 9 is a graph illustrating a relationship in the accumulation amount of [$^{18}$F]BCPP-BF between the liver and the kidneys.

As shown in FIGS. 5 to 9, the amount of [$^{18}$F]BCPP-BF accumulated in each tissue and organ (brain, heart, brown adipocytes, pancreas, liver, and kidneys) also showed a significant correlation (positive correlation) between any two of the tissues and organs. It is thought that this means that interactions between the tissues and organs can be detected by determining whether there is a correlation in the amount of [$^{18}$F]BCPP-BF accumulated.

Figure 21:
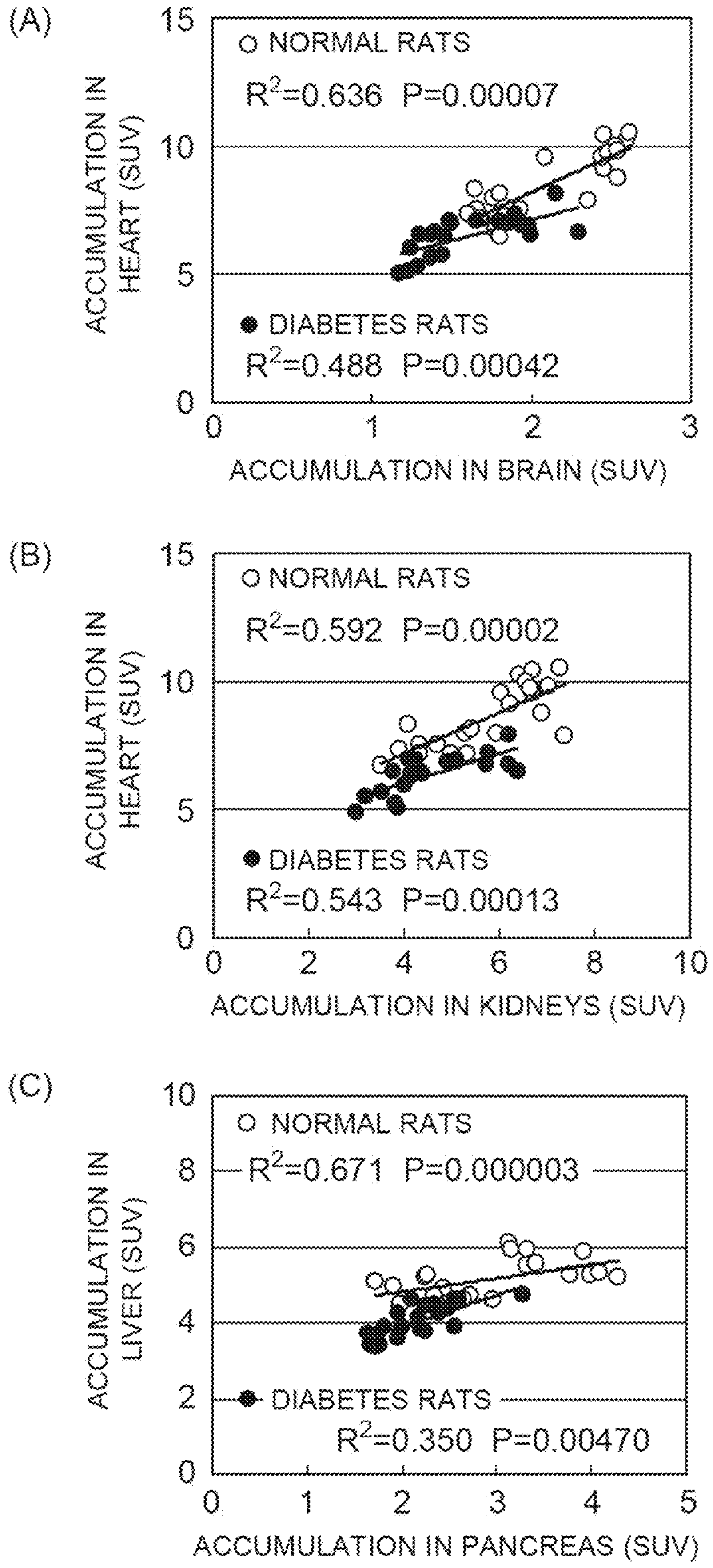
FIG. 21(A) is a graph illustrating a relationship in the accumulation amount of [$^{18}$F]BCPP-BF between the brain and the heart of each of the normal rats and the diabetes model rats.
FIG. 21(B) is a graph illustrating a relationship in the accumulation amount of [$^{18}$F]BCPP-BF between the kidneys and the heart of each of the normal rats and the diabetes model rats.
FIG. 21(C) is a graph illustrating a relationship in the accumulation amount of [$^{18}$F]BCPP-BF between the pancreas and the liver of each of the normal rats and the diabetes model rats.

FIG. 21 shows graphs in which a relationship (FIG. 21(A)) in the amount of [$^{18}$F]BCPP-BF accumulated in the brain and the heart, a relationship (FIG. 21(B)) in the amount of [$^{18}$F]BCPP-BF accumulated in the kidneys and the heart, and a relationship (FIG. 21(C)) in the amount of [$^{18}$F]BCPP-BF accumulated in the pancreas and the liver were plotted separately for the normal rats (lean rats) and the diabetes model rats (fatty rats). As shown in FIG. 21, although there was a trend that there was a slight difference in the slopes of the graphs between the normal rats and the diabetes model rats, when it is considered together with the results of FIGS. 5 and 9, it can be seen that there is a favorable correlation between the tissues and organs and that the condition of a subject may not be considered, even in a case where accumulation amount data of the normal rats and the diabetes model rats at all weeks of age was used.

Figure 10:
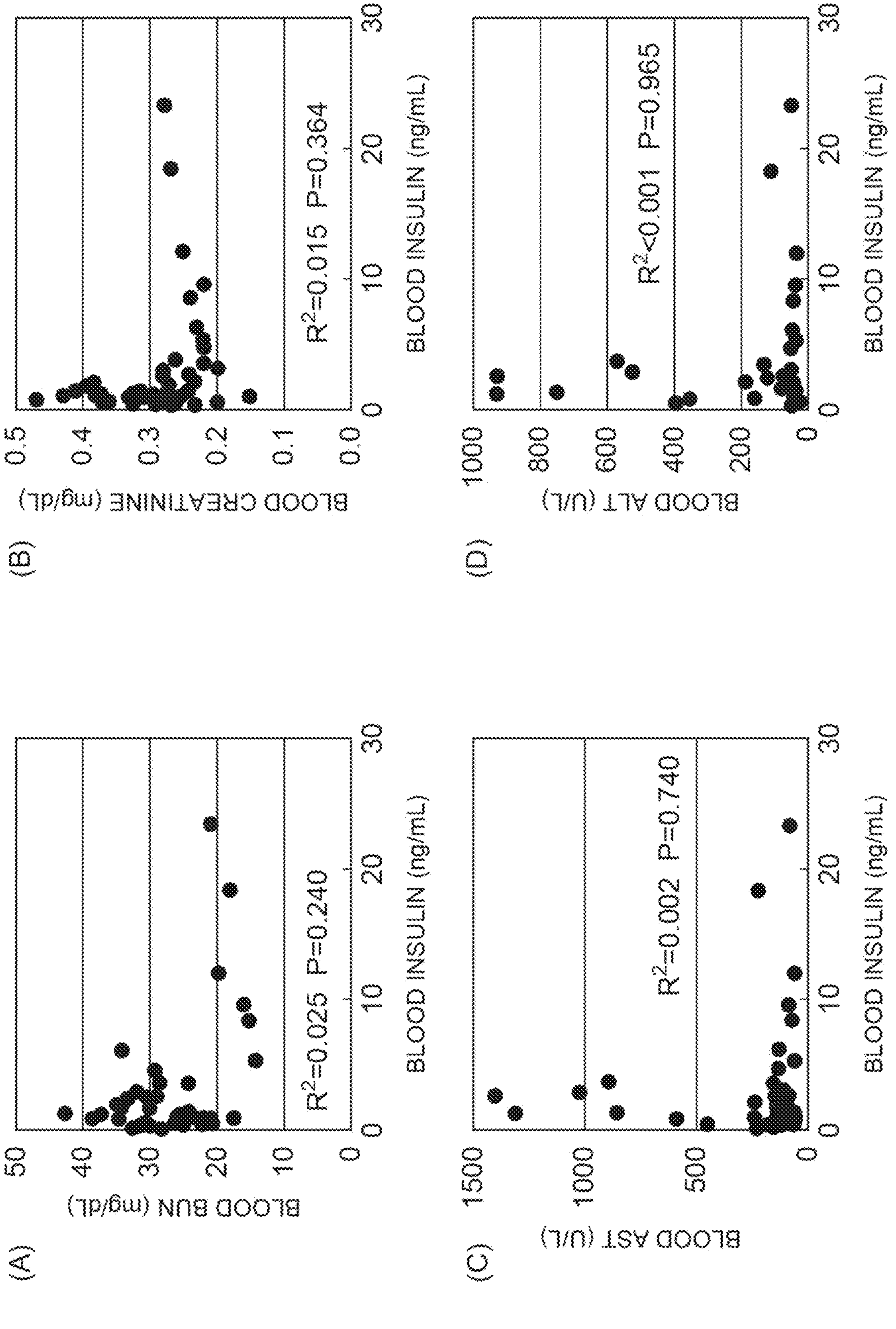
FIG. 10(A) is a graph illustrating a relationship between blood insulin concentration and blood BUN concentration.
FIG. 10(B) is a graph illustrating a relationship between blood insulin concentration and blood creatinine concentration.
FIG. 10(C) is a graph illustrating a relationship between blood insulin concentration and blood AST concentration.
FIG. 10(D) is a graph illustrating a relationship between blood insulin concentration and blood ALT concentration.
Figure 11:
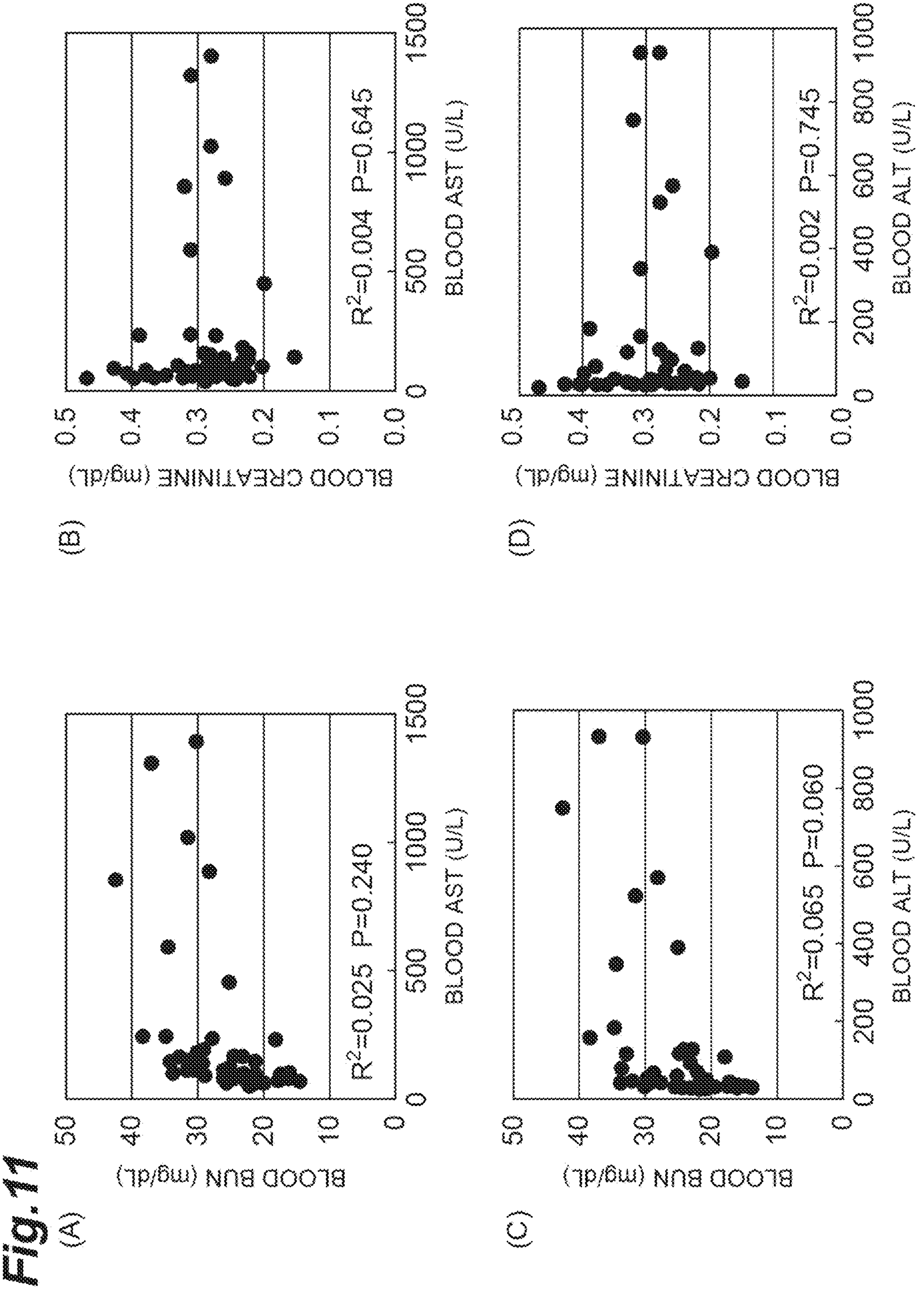
FIG. 11(A) is a graph illustrating a relationship between blood AST concentration and blood BUN concentration.
FIG. 11(B) is a graph illustrating a relationship between blood AST concentration and blood creatinine concentration.
FIG. 11(C) is a graph illustrating a relationship between blood ALT concentration and blood BUN concentration.
FIG. 11(D) is a graph illustrating a relationship between blood ALT concentration and blood creatinine concentration.
Figure 12:
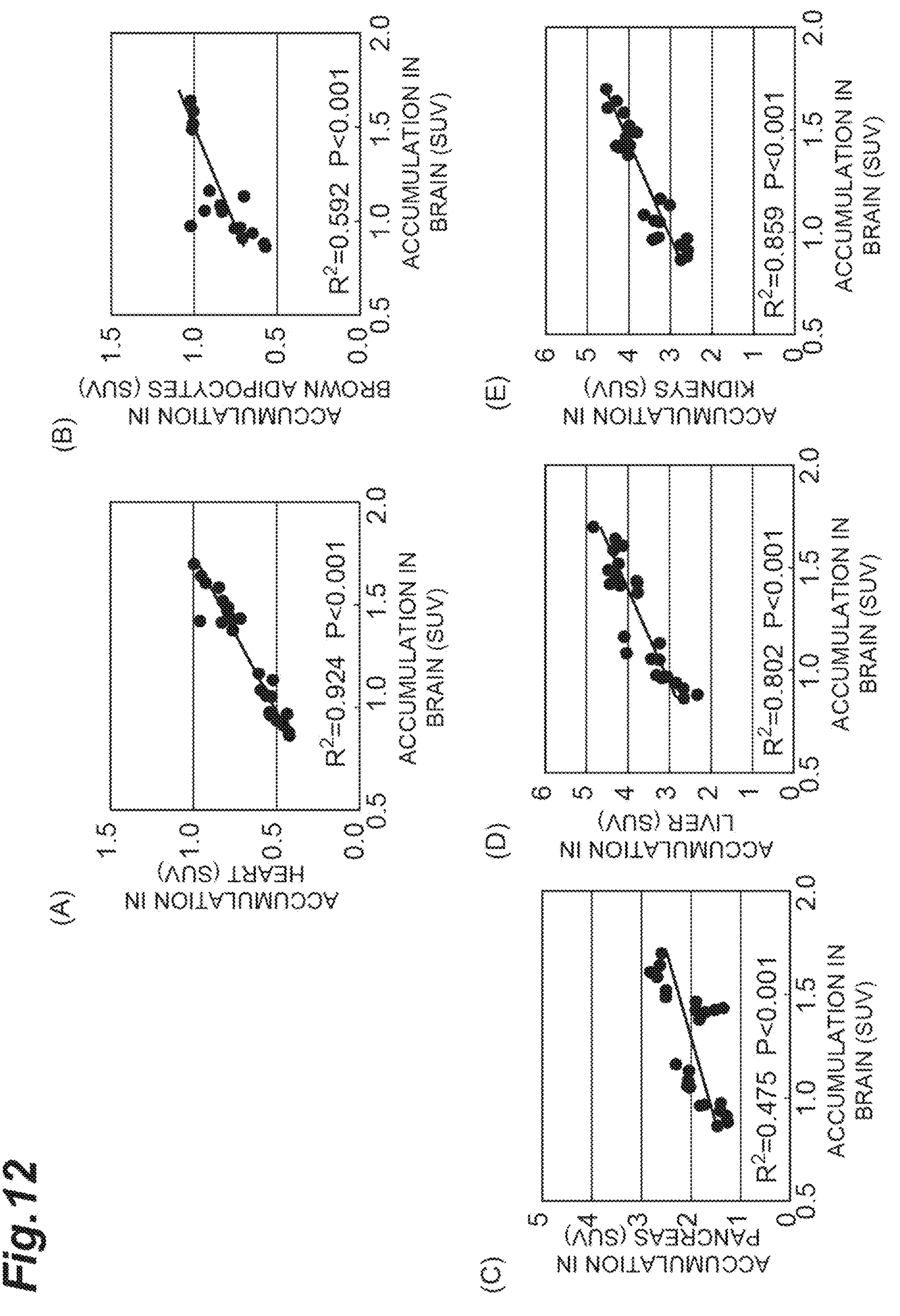
FIG. 12(A) is a graph illustrating a relationship in the accumulation amount of [$^{18}$F]BCPP-EF between the brain and the heart.
FIG. 12(B) is a graph illustrating a relationship in the accumulation amount of [$^{18}$F]BCPP-EF between the brain and brown adipocytes.
FIG. 12(C) is a graph illustrating a relationship in the accumulation amount of [$^{18}$F]BCPP-EF between the brain and the pancreas.
FIG. 12(D) is a graph illustrating a relationship in the accumulation amount of [$^{18}$F]BCPP-EF between the brain and the liver.
FIG. 12(E) is a graph illustrating a relationship in the accumulation amount of [$^{18}$F]BCPP-EF between the brain and the kidneys.
Figure 13:
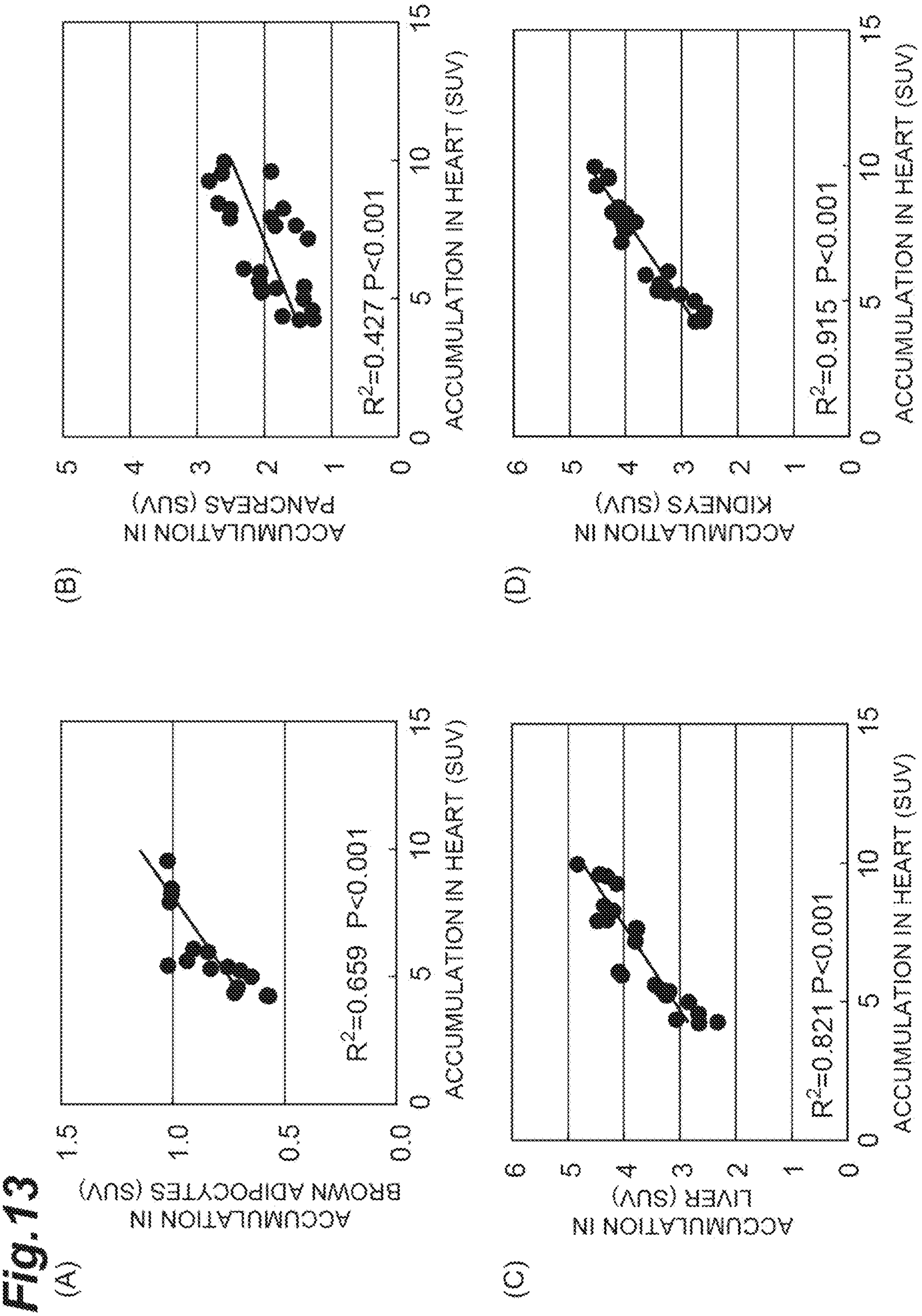
FIG. 13(A) is a graph illustrating a relationship in the accumulation amount of [$^{18}$F]BCPP-EF between the heart and brown adipocytes.
FIG. 13(B) is a graph illustrating a relationship in the accumulation amount of [$^{18}$F]BCPP-EF between the heart and the pancreas.
FIG. 13(C) is a graph illustrating a relationship in the accumulation amount of [$^{18}$F]BCPP-EF between the heart and the liver.
FIG. 13(D) is a graph illustrating a relationship in the accumulation amount of [$^{18}$F]BCPP-EF between the heart and the kidneys.
Figure 14:
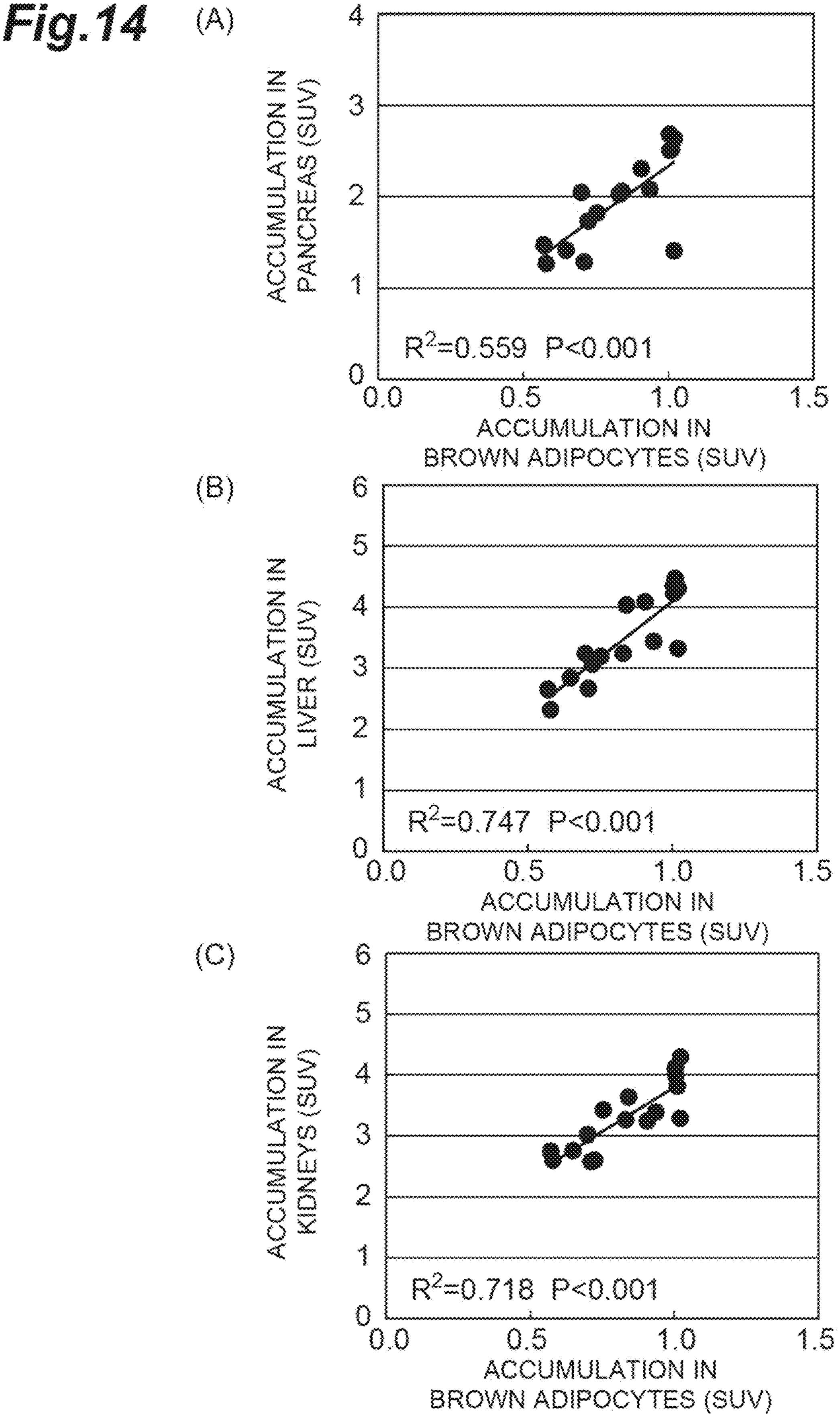
FIG. 14(A) is a graph illustrating a relationship in the accumulation amount of [$^{18}$F]BCPP-EF between brown adipocytes and the pancreas.
FIG. 14(B) is a graph illustrating a relationship in the accumulation amount of [$^{18}$F] BCPP-EF between brown adipocytes and the liver.
FIG. 14(C) is a graph illustrating a relationship in the accumulation amount of [$^{18}$F]BCPP-EF between brown adipocytes and the kidneys.
Figure 15:
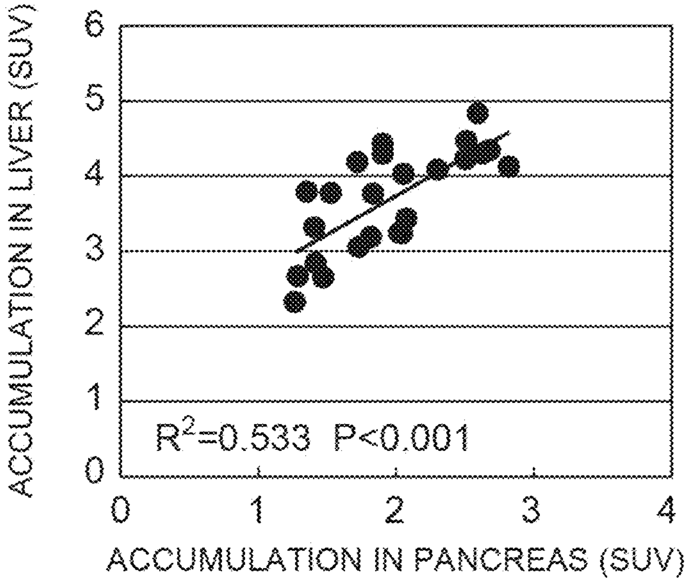
FIG. 15(A) is a graph illustrating a relationship in the accumulation amount of [$^{18}$F]BCPP-EF between the pancreas and the liver.
FIG. 15(B) is a graph illustrating a relationship in the accumulation amount of [$^{18}$F]BCPP-EF between the pancreas and the kidneys.
Figure 15:
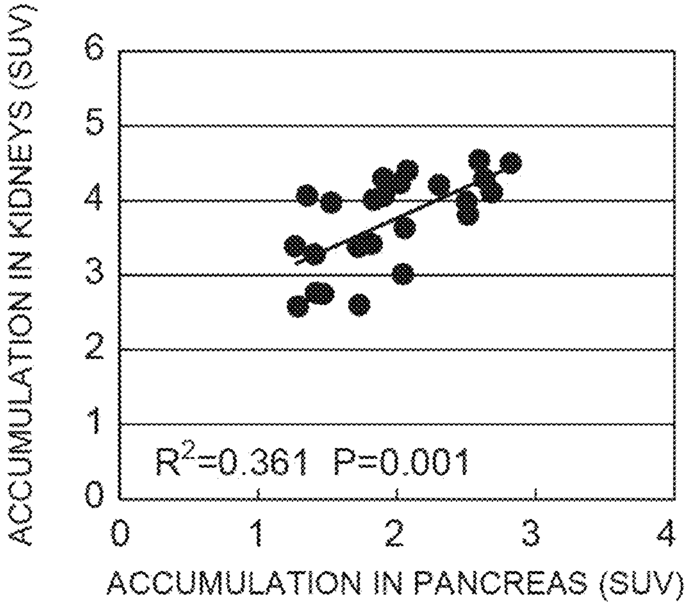

In addition, FIGS. 10 and 11 are graphs illustrating relationships between biochemical indicators. In FIGS. 10 and 11, the biochemical indicators in the fatty rats and the biochemical indicators in the lean rats are plotted without distinction. Here, FIG. 10(A) is a graph illustrating a relationship between blood insulin concentration and blood BUN concentration. FIG. 10(B) is a graph illustrating a relationship between blood insulin concentration and blood creatinine concentration. FIG. 10(C) is a graph illustrating a relationship between blood insulin concentration and blood AST concentration. FIG. 10(D) is a graph illustrating a relationship between blood insulin concentration and blood ALT concentration. FIG. 11(A) is a graph illustrating a relationship between blood AST concentration and blood BUN concentration. FIG. 11(B) is a graph illustrating a relationship between blood AST concentration and blood creatinine concentration. FIG. 11(C) is a graph illustrating a relationship between blood ALT concentration and blood BUN concentration. FIG. 11(D) is a graph illustrating a relationship between blood ALT concentration and blood creatinine concentration.

As shown in FIGS. 10 and 11, no significant correlation was observed between any of the biochemical indicators. These results mean that interactions between tissues and organs that cannot be detected through conventional evaluation methods using biochemical indicators can be detected using the agent for detecting an interaction between tissues and organs according to the present invention.

Test Example 2: Detection of Interaction Between Tissues and Organs (2)

(Synthesis of PET Probe)

[$^{18}$F]BCPP-EF represented by the following formula was synthesized according to the method disclosed in the examples of PCT International Publication No. WO2014/030709. The final product obtained had a radiochemical purity of 99.8% and a specific radioactivity of 73.6 GBq/μmol.

[Chem. 10]

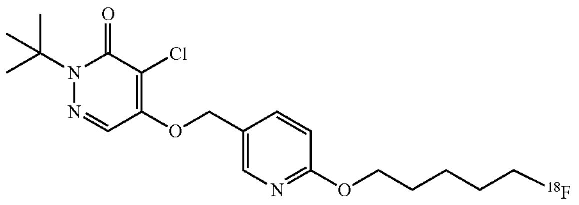

(Evaluation of function of each tissue and organ in Type 2 Diabetes Model Rats)

The same operation as in Test Example 1 was performed except that [$^{18}$F]BCPP-EF was used instead of [$^{18}$F]BCPP-BF, and the amount (SUV) of radioactivity accumulated of [$^{18}$F]BCPP-EF in each tissue and organ was calculated. In addition, the presence or absence of a correlation between the tissues and organs with respect to the amount (SUV) of radioactivity accumulated of [$^{18}$F]BCPP-EF in the tissues and organs was evaluated.

(Results)

FIGS. 12 to 16 are graphs illustrating relationships in the accumulation amount of [$^{18}$F]BCPP-EF between tissues and organs. In FIGS. 12 to 16, the accumulation amount in the fatty rats and the accumulation amount in the lean rats are plotted without distinction.

Figure 16:
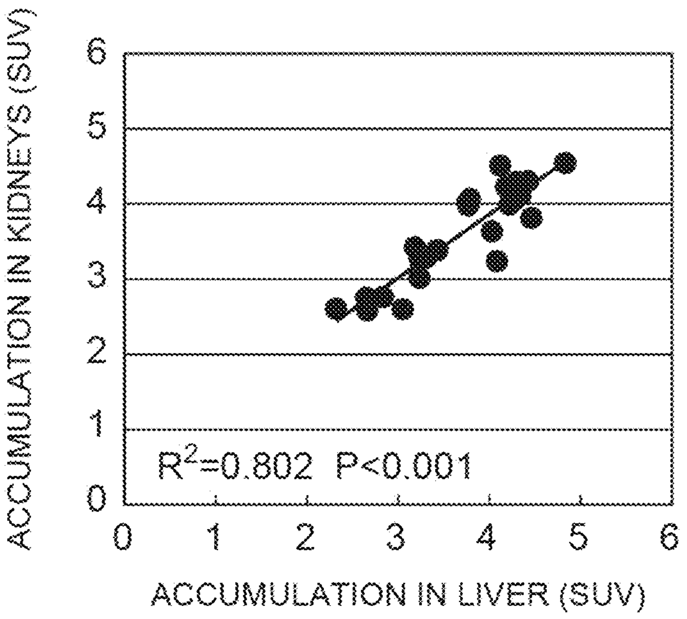
FIG. 16 is a graph illustrating a relationship in the accumulation amount of [$^{18}$F]BCPP-EF between the liver and the kidneys.
Figure 17:
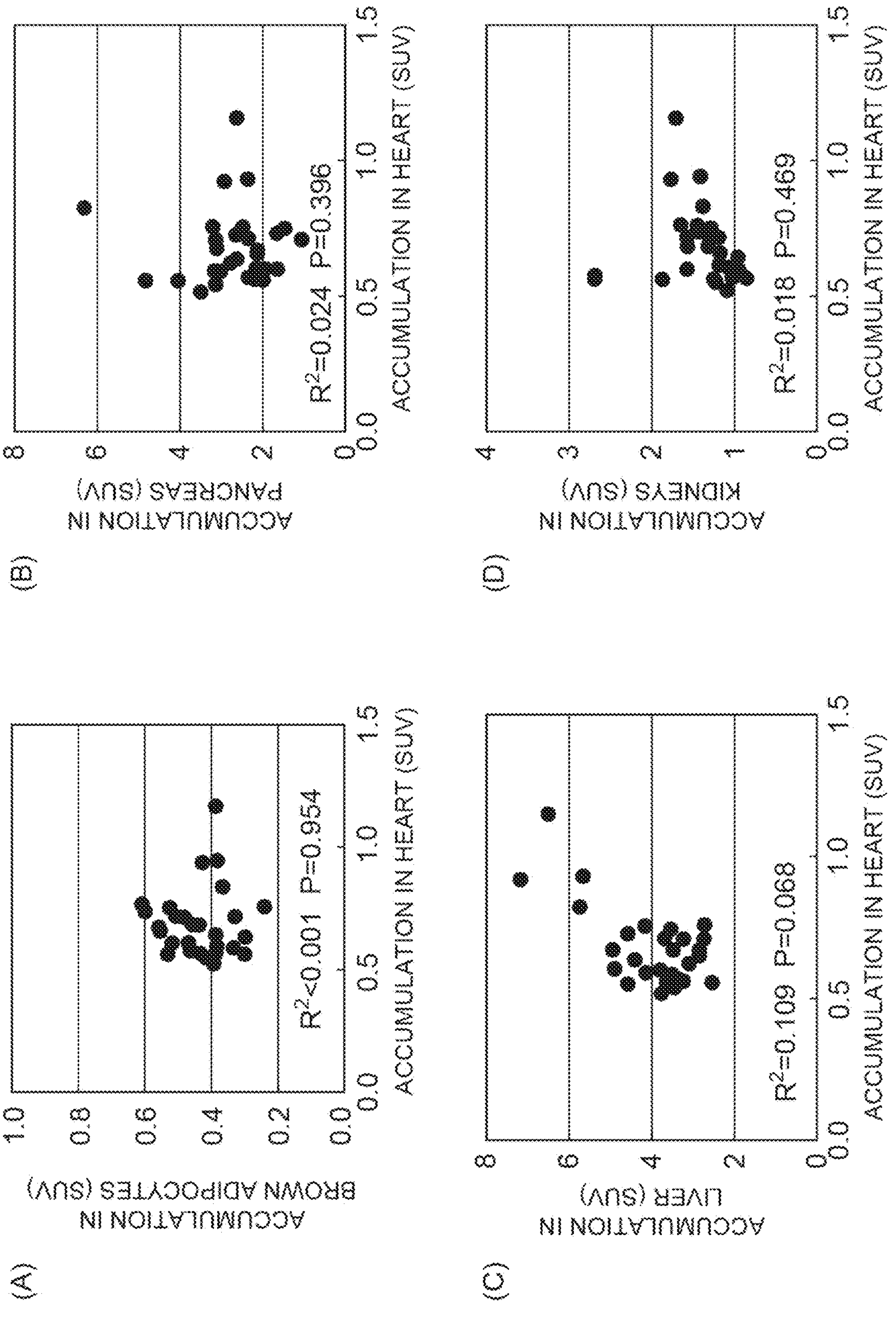
FIG. 17(A) is a graph illustrating a relationship in the accumulation amount of [$^{11}$C]HM between the heart and brown adipocytes.
FIG. 17(B) is a graph illustrating a relationship in the accumulation amount of [$^{11}$C]HM between the heart and the pancreas.
FIG. 17(C) is a graph illustrating a relationship in the accumulation amount of [$^{11}$C]HM between the heart and the liver.
FIG. 17(D) is a graph illustrating a relationship in the accumulation amount of [$^{11}$C]HM between the heart and the kidneys.
Figure 18:
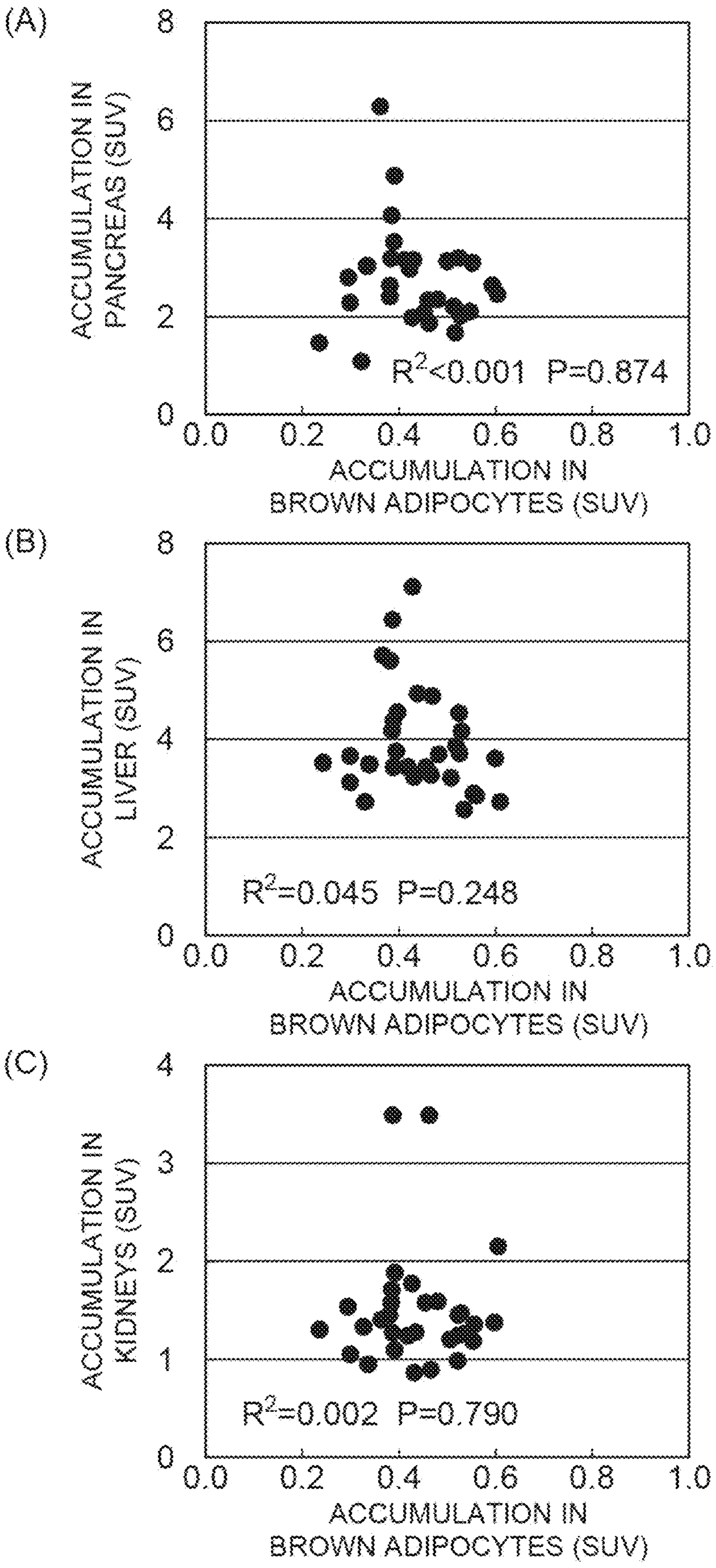
FIG. 18(A) is a graph illustrating a relationship in the accumulation amount of [$^{11}$C]HM between brown adipocytes and the pancreas.
FIG. 18(B) is a graph illustrating a relationship in the accumulation amount of [$^{11}$C]HM between brown adipocytes and the liver.
FIG. 18(C) is a graph illustrating a relationship in the accumulation amount of [$^{11}$C]HM between brown adipocytes and the kidneys.
Figure 19:
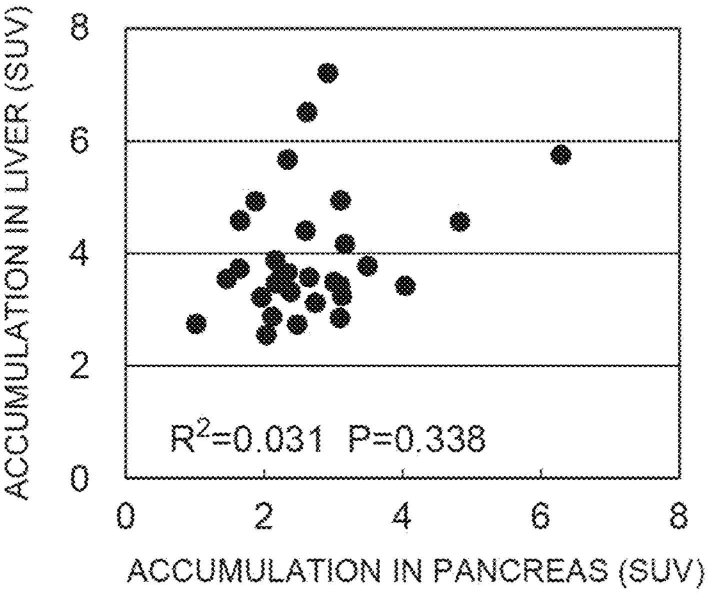
FIG. 19(A) is a graph illustrating a relationship in the accumulation amount of [$^{11}$C]HM between the pancreas and the liver.
FIG. 19(B) is a graph illustrating a relationship in the accumulation amount of [$^{11}$C]HM between the pancreas and the kidneys.
Figure 19:
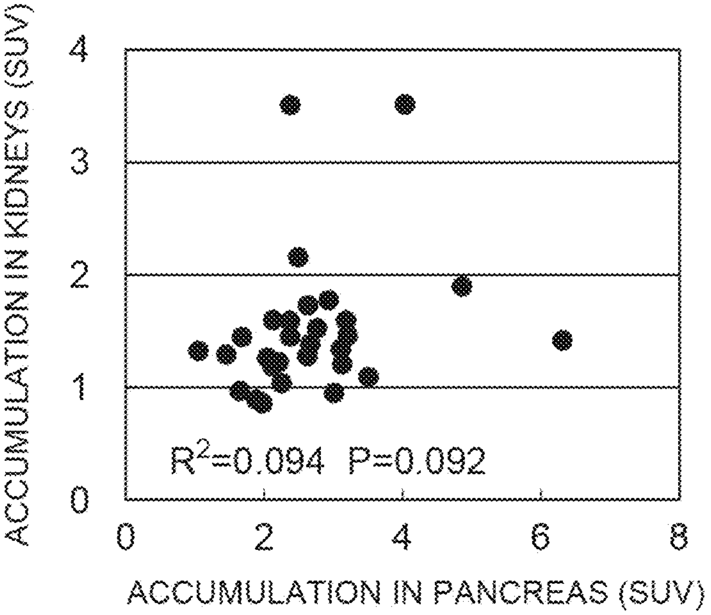

FIG. 12(A) is a graph illustrating a relationship in the accumulation amount of [$^{18}$F]BCPP-EF between the brain and the heart. FIG. 12(B) is a graph illustrating a relationship in the accumulation amount of [$^{18}$F]BCPP-EF between the brain and brown adipocytes. FIG. 12(C) is a graph illustrating a relationship in the accumulation amount of [$^{18}$F]BCPP-EF between the brain and the pancreas. FIG. 12(D) is a graph illustrating a relationship in the accumulation amount of [$^{18}$F]BCPP-EF between the brain and the liver. FIG. 12(E) is a graph illustrating a relationship in the accumulation amount of [$^{18}$F]BCPP-EF between the brain and the kidneys. FIG. 13(A) is a graph illustrating a relationship in the accumulation amount of [$^{18}$F]BCPP-EF between the heart and brown adipocytes. FIG. 13(B) is a graph illustrating a relationship in the accumulation amount of [$^{18}$F]BCPP-EF between the heart and the pancreas. FIG. 13(C) is a graph illustrating a relationship in the accumulation amount of [$^{18}$F]BCPP-EF between the heart and the liver. FIG. 13(D) is a graph illustrating a relationship in the accumulation amount of [$^{18}$F]BCPP-EF between the heart and the kidneys. FIG. 14(A) is a graph illustrating a relationship in the accumulation amount of [$^{18}$F]BCPP-EF between brown adipocytes and the pancreas. FIG. 14(B) is a graph illustrating a relationship in the accumulation amount of [$^{18}$F]BCPP-EF between brown adipocytes and the liver. FIG. 14(C) is a graph illustrating a relationship in the accumulation amount of [$^{18}$F]BCPP-EF between brown adipocytes and the kidneys. FIG. 15(A) is a graph illustrating a relationship in the accumulation amount of [$^{18}$F]BCPP-EF between the pancreas and the liver. FIG. 15(B) is a graph illustrating a relationship in the accumulation amount of [$^{18}$F]BCPP-EF between the pancreas and the kidneys. FIG. 16 is a graph illustrating a relationship in the accumulation amount of [$^{18}$F]BCPP-EF between the liver and the kidneys.

As shown in FIGS. 12 to 16, the amount of [$^{18}$F]BCPP-EF accumulated in each tissue and organ (brain, heart, brown adipocytes, pancreas, liver, and kidneys) also showed a significant correlation (positive correlation) between any two of the tissues and organs. It is thought that this means that interactions between the tissues and organs can be detected by determining whether there is a correlation in the amount of [$^{18}$F]BCPP-EF accumulated.

Test Example 3: Detection of Interaction Between Tissues and Organs (3)

(Synthesis of PET Probe)

[$^{11}$C]HM represented by the following formula was synthesized as a PET probe for comparison. [$^{11}$C]HM is a PET probe that detects active oxygen species.

[Chem. 11]

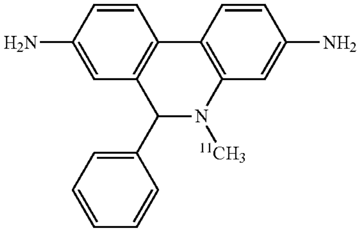

[$^{11}$C]HM was synthesized according to the following scheme.

[Chem. 12]

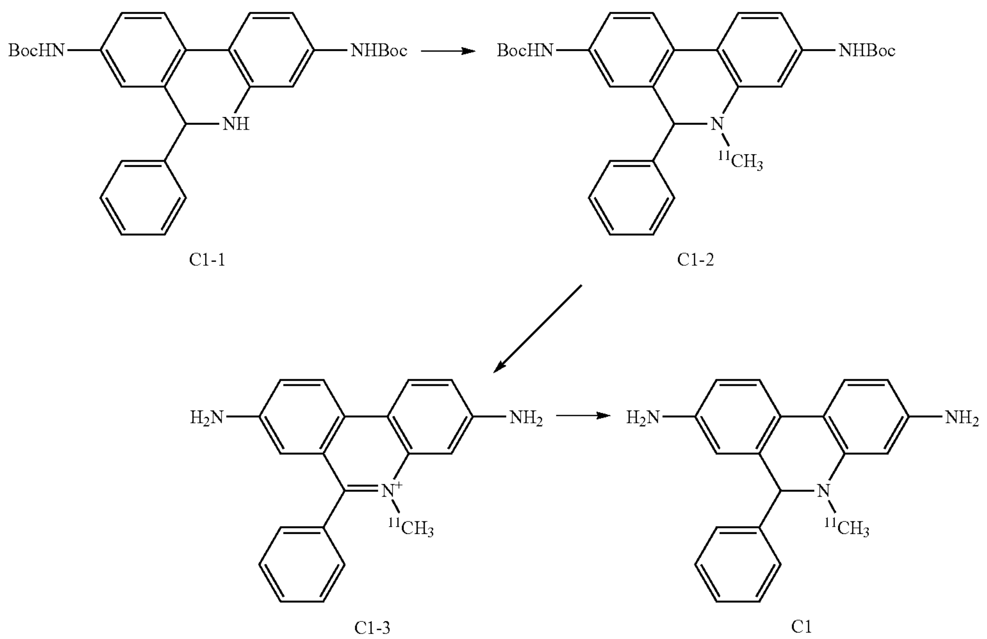

A target filled with pure nitrogen gas (grade G, manufactured by Japan Fine Products Co., Ltd.) was irradiated with protons accelerated to 18 MeV at a current value of about 20 ρA using a cyclotron (HM-18, manufactured by Sumitomo Heavy Industries, Ltd.). [$^{11}$C]$CO_2$ produced by the $^{14}$N(p, α)$^{11}$C nuclear reaction was recovered in an automatic synthesizer (manufactured by Sumitomo Heavy Industries, Ltd.) and introduced into 500 μL of a cooled 0.1M $LiAlH_4$/tetrahydrofuran (THF) solution (manufactured by ABX advanced biochemical compounds). After distilling off THF, 0.5 mL of hydroiodic acid (manufactured by Nacalai Tesque, Inc.) was added, the produced [$^{11}$C]methyl iodide was distilled and passed over a silver triflate column heated to 200° C. to convert the [$^{11}$C]methyl iodide to [$^{11}$C]methyl triflate.

1.5 mg of a precursor (compound C1-1) was dissolved in 0.2 mL of methyl ethyl ketone, the above-described [$^{11}$C] methyl triflate was introduced, and methylation was performed at 50° C. for 3 minutes to synthesize a compound C1-2. Subsequently, 6 N hydrochloric acid/ethanol=133 μL/320 μL was added, and a deprotection reaction was carried out at 80° C. for 4 minutes to synthesize a compound $C_{1-3}$. Subsequently, sodium borohydride/1 N sodium hydroxide=8 mg/820 μL was added thereto to synthesize [$^{11}$C]HM (compound C1).

The reaction solution was fractionated through high-performance liquid chromatography (column: YMC Pack Pro C18, 10*250 mm, 5 μm (YMC, USA), mobile phase: 20 mM phosphate buffer solution at a pH of 2.8 (0.5% ascorbic acid+0.05% $NaHSO_3$)/acetonitrile=500/500, flow rate: 6 mL/min, detection wavelength: 254 nm). The solvent was distilled off, and 0.1% Tween 80/physiological saline was added to the residue to obtain a final preparation.

The radioactivity of the final preparation was measured with a curie meter (IGC-7 manufactured by Hitachi Aloka Medical, Ltd.), and a part of it was analyzed through analytical high-performance liquid chromatography (column: Finepak C18-S, 4.6*150 mm (manufactured by JASCO Corporation), mobile phase: acetonitrile (manufactured by Wako Pure Chemical Industries, Ltd.)/30 mM ammonium acetate (manufactured by Nacalai Tesque, Inc.)/acetate (manufactured by Wako Pure Chemical Industries, Ltd.)=500/500/2, flow rate: 2 mL/minute, detection wavelength: 254 nm) (n=4). The results are as follows.

Production amount: 2.54±1.18 GBq (EOS)

Average specific radioactivity: 50.4±16.9 GBq/μmol (EOS)

Average synthesis time: 30.1±3.8 minutes (Evaluation of Function of Each Tissue and Organ in Type 2 Diabetes Model Rats)

The same operation as in Test Example 1 was performed except that [$^{11}$C]HM was used instead of [$^{18}$F]BCPP-BF, and the amount (SUV) of radioactivity accumulated of [$^{11}$C]HM in each tissue and organ was calculated. In addition, the presence or absence of a correlation between the tissues and organs with respect to the amount (SUV) of radioactivity accumulated of [$^{11}$C]HM in the tissues and organs was evaluated.

(Results)

FIGS. 17 to 20 are graphs illustrating relationships in the accumulation amount of [$^{11}$C]HM between tissues and organs. In FIGS. 17 to 20, the accumulation amount in the fatty rats and the accumulation amount in the lean rats are plotted without distinction.

Figure 20:
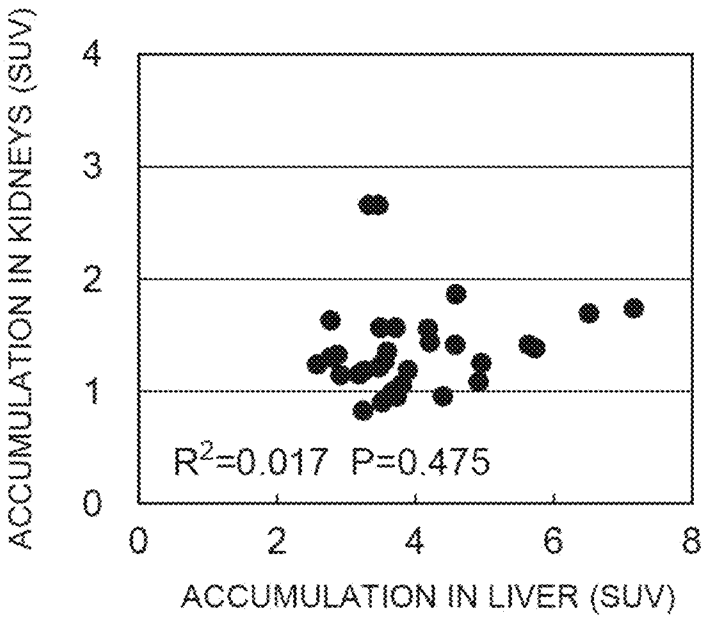
FIG. 20 is a graph illustrating a relationship in the accumulation amount of [$^{11}$C]HM between the liver and the kidneys.

FIG. 17(A) is a graph illustrating a relationship in the accumulation amount of [$^{11}$C]HM between the heart and brown adipocytes. FIG. 17(B) is a graph illustrating a relationship in the accumulation amount of [$^{11}$C]HM between the heart and the pancreas. FIG. 17(C) is a graph illustrating a relationship in the accumulation amount of [$^{11}$C]HM between the heart and the liver. FIG. 17(D) is a graph illustrating a relationship in the accumulation amount of [$^{11}$C]HM between the heart and the kidneys. FIG. 18(A) is a graph illustrating a relationship in the accumulation amount of [$^{11}$C]HM between brown adipocytes and the pancreas. FIG. 18(B) is a graph illustrating a relationship in the accumulation amount of [$^{11}$C]HM between brown adipocytes and the liver. FIG. 18(C) is a graph illustrating a relationship in the accumulation amount of [$^{11}$C]HM between brown adipocytes and the kidneys. FIG. 19(A) is a graph illustrating a relationship in the accumulation amount of [$^{11}$C]HM between the pancreas and the liver. FIG. 19(B) is a graph illustrating a relationship in the accumulation amount of [$^{11}$C]HM between the pancreas and the kidneys. FIG. 20 is a graph illustrating a relationship in the accumulation amount of [$^{11}$C]HM between the liver and the kidneys.

As shown in FIGS. 17 to 20, when [$^{11}$C]HM which is a PET probe that detects active oxygen species was used, no significant correlation in the accumulation amount was observed between any of the tissues and organs.

From the results of Test Examples 1 to 3, it can be understood that, by using a probe accumulated specifically for MC-I, it is possible to detect interactions between tissues and organs based on the amount of probe accumulated.

The invention claimed is:

1. A method for detecting an interaction between tissues and organs, comprising:

administering a detection agent to a subject; wherein the detection agent comprises a compound represented by General Formula (1-0) as an active component, (1-0)

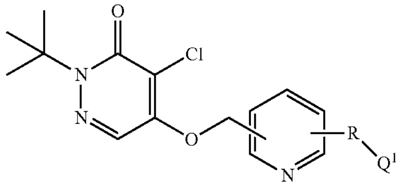

and wherein, in General Formula (1-0), R represents $—O(CH_2)_n—$, $—O(CH_2)_nOC_2H_4—$, $—CH_2O(CH_2)_n—$, or $—CH_2O(CH_2)_nOC_2H_4—$, n represents an integer of 1 to 5, and $Q^1$ represents F or $—OCH_3$, detecting the active component accumulated in a plurality of different types of tissues and/or organs to be evaluated;

quantitatively analyzing an amount of the active component accumulated in the plurality of different types of tissues and/or organs to be evaluated; and determining whether there is a correlation in the accumulation amount of the active component between the plurality of different types of tissues and/or organs to be evaluated based on the quantitatively analyzed results.

2. A tissue/organ interaction detection device comprising:

acquisition means for acquiring detection data on the active component accumulated in a plurality of different types of tissues and/or organs to be evaluated which is obtained by measuring the subject to which a detection agent is administered; wherein the detection agent comprises a compound represented by General Formula (1-0) as an active component, (1-0)

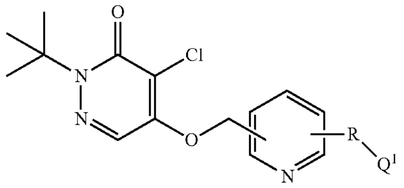

and wherein, in General Formula (1-0), R represents $—O(CH_2)_n—$, $—O(CH_2)_nOC_2H_4—$, $—CH_2O(CH_2)_n—$, or $—CH_2O(CH_2)_nOC_2H_4—$, n represents an integer of 1 to 5, and $Q^1$ represents F or $—OCH_3$;

quantitative analysis means for quantitatively analyzing the amount of the active component accumulated in the plurality of different types of tissues and/or organs to be evaluated from the acquired detection data; and determination means for determining whether there is a correlation in the accumulation amount of the active component between the plurality of different types of tissues and/or organs to be evaluated based on the quantitatively analyzed results.

3. A tissue/organ interaction detection program for causing a computer to function as:

acquisition means for acquiring detection data on the active component accumulated in a plurality of different types of tissues and/or organs to be evaluated which is obtained by measuring the subject to which a detection agent is administered; wherein the detection agent comprises a compound represented by General Formula (1-0) as an active component, (1-0)

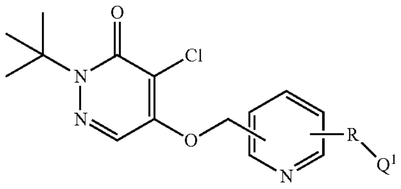

and wherein, in General Formula (1-0), R represents $—O(CH_2)_n—$, $—O(CH_2)_nOC_2H_4—$, $—CH_2O(CH_2)_n—$, or $—CH_2O(CH_2)_nOC_2H_4—$, n represents an integer of 1 to 5, and $Q^1$ represents F or $—OCH_3$;

quantitative analysis means for quantitatively analyzing the amount of the active component accumulated in the plurality of different types of tissues and/or organs to be evaluated from the acquired detection data; and determination means for determining whether there is a correlation in the accumulation amount of the active component between the plurality of different types of tissues and/or organs to be evaluated based on the quantitatively analyzed results.

4. The method according to claim 1, wherein the active component is a compound represented by General Formula (1-0'), (1-0')

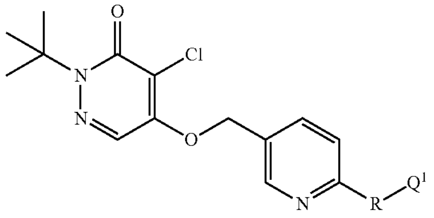

and wherein, in General Formula (1-0'), R, n, and $Q^1$ are synonymous with R, n, and $Q^1$ in General Formula (1-0).

5. The method according to claim 1, wherein the active component is a compound represented by General Formula (1-0") or a compound represented by General Formula (1-0'''), (1-0")

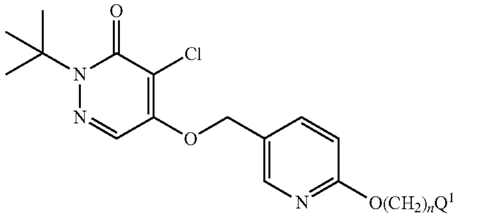

(1-0"')

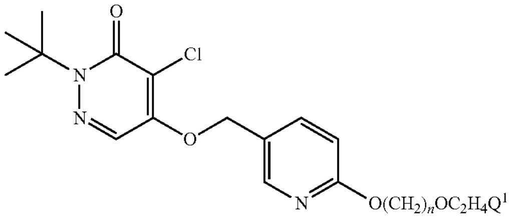

and wherein, in General Formulae (1-0") and (1-0"'), n and $Q^1$ are synonymous with n and $Q^1$ in General Formula (1-0).

6. The method according to claim 1, wherein the active component is a compound represented by Formula (1") below or a compound represented by Formula (1"') below, (1")

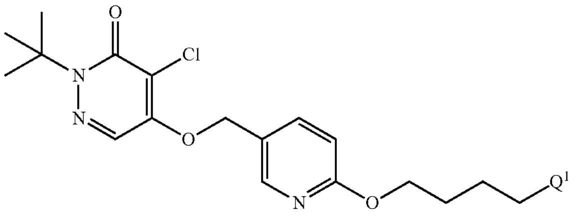

(1"')

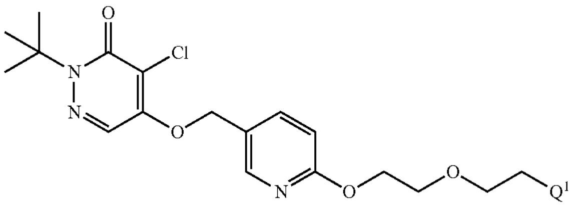

and wherein, in Formula (1") and (1"'), $Q^1$ is synonymous with $Q^1$ in General Formula (1-0).

7. The method according to claim 1, wherein $Q^1$ is $^{18}F$ or $—O^{11}CH_3$.

8. The tissue/organ interaction detection device according to claim 2, wherein the active component is a compound represented by General Formula (1-0'), (1-0')

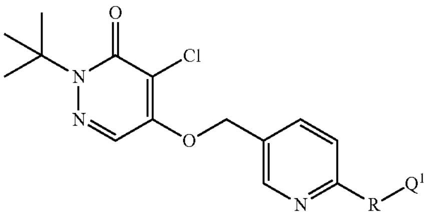

and wherein, in General Formula (1-0'), R, n, and $Q^1$ are synonymous with R, n, and $Q^1$ in General Formula (1-0).

9. The tissue/organ interaction detection device according to claim 2, wherein the active component is a compound represented by General Formula (1-0") or a compound represented by General Formula (1-0"'), (1-0")

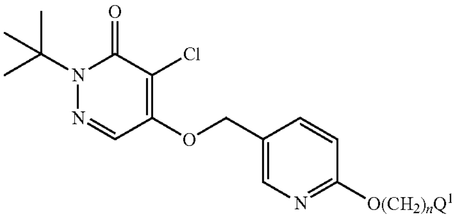

(1-0"')

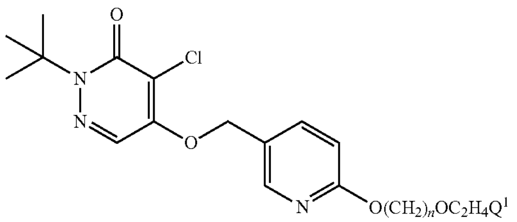

and wherein, in General Formulae (1-0") and (1-0"'), n and $Q^1$ are synonymous with n and $Q^1$ in General Formula (1-0).

10. The tissue/organ interaction detection device according to claim 2, wherein the active component is a compound represented by Formula (1") below or a compound represented by Formula (1"') below, (1")

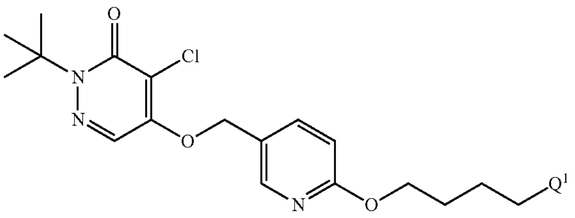

-continued (1''')

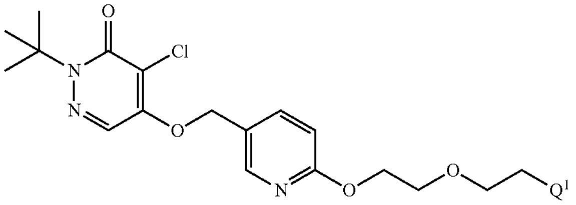

and wherein, in Formula (1") and (1'"), $Q^1$ is synonymous with $Q^1$ in General Formula (1-0).

11. The tissue/organ interaction detection device according to claim 2, wherein $Q^1$ is $^{18}F$ or —$O^{11}CH_3$.

12. The tissue/organ interaction detection program according to claim 3, wherein the active component is a compound represented by General Formula (1-0'), (1-0')

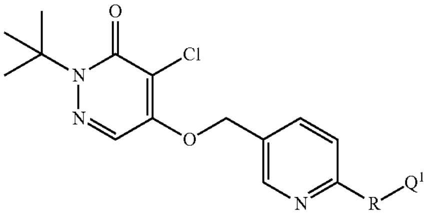

and wherein, in General Formula (1-0'), R, n, and $Q^1$ are synonymous with R, n, and $Q^1$ in General Formula (1-0).

13. The tissue/organ interaction detection program according to claim 3, wherein the active component is a compound represented by General Formula (1-0") or a compound represented by General Formula (1-0'"), (1-0'')

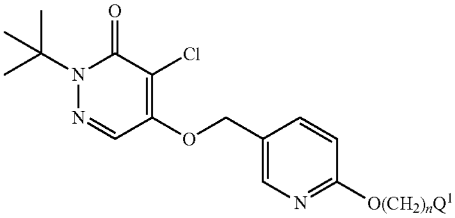

-continued (1-0''')

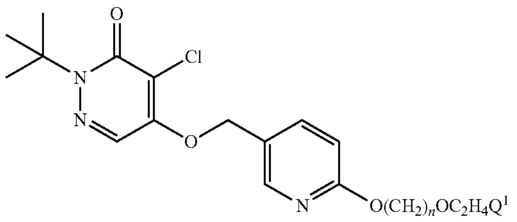

and wherein, in General Formulae (1-0") and (1-0'"), n and $Q^1$ are synonymous with n and $Q^1$ in General Formula (1-0).

14. The tissue/organ interaction detection program according to claim 3, wherein the active component is a compound represented by Formula (1") below or a compound represented by Formula (1'") below, (1'')

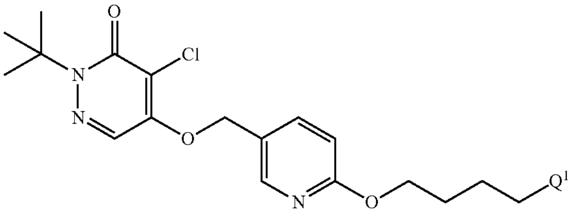

(1''')

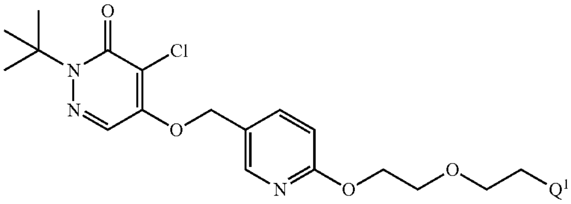

and wherein, in Formula (1") and (1'"), $Q^1$ is synonymous with $Q^1$ in General Formula (1-0).

15. The tissue/organ interaction detection program according to claim 3, wherein $Q^1$ is $^{18}F$ or —$O^{11}CH_3$.

* * * * *